(12) United States Patent
Mohapatra et al.

(10) Patent No.: US 9,096,829 B2
(45) Date of Patent: Aug. 4, 2015

(54) HUMAN MAST CELL LINE AND USES THEREOF

(75) Inventors: Shyam S. Mohapatra, Lutz, FL (US); Mark Glaum, Lutz, FL (US); Guoqing Liu, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 13/255,599

(22) PCT Filed: Mar. 12, 2010

(86) PCT No.: PCT/US2010/027220
§ 371 (c)(1),
(2), (4) Date: Nov. 30, 2011

(87) PCT Pub. No.: WO2010/105215
PCT Pub. Date: Sep. 16, 2010

(65) Prior Publication Data
US 2012/0093781 A1   Apr. 19, 2012

Related U.S. Application Data

(60) Provisional application No. 61/210,046, filed on Mar. 12, 2009.

(51) Int. Cl.
C12N 1/00 (2006.01)
C12N 5/0787 (2010.01)
G01N 33/50 (2006.01)

(52) U.S. Cl.
CPC .......... *C12N 5/0642* (2013.01); *G01N 33/5047* (2013.01); *C12N 2501/125* (2013.01); *C12N 2501/23* (2013.01); *C12N 2510/00* (2013.01)

(58) Field of Classification Search
None
See application file for complete search history.

(56) References Cited

U.S. PATENT DOCUMENTS

| 4,940,782 | A | 7/1990 | Rup et al. | |
|---|---|---|---|---|
| 2006/0105398 | A1* | 5/2006 | Rossi | 435/7.2 |
| 2007/0015280 | A1 | 1/2007 | Rossi | |
| 2007/0178075 | A1 | 8/2007 | Chaudhry et al. | |
| 2010/0260725 | A1 | 10/2010 | Mohapatra et al. | |

OTHER PUBLICATIONS

Piliponsky et al. "Non-IgE-dependent activation of human lung- and cord blood-derived mast cells is induced by eosinophil major basic protein and modulated by the membrane form of stem cell factor", Blood 101: 1898-1904, 2002.*
Ra et al. "Complete structure of the mouse mast cell receptor of IgE (FceR1) and surface expression of chimeric receptors (rat-mouse-human) on transfected cells" 264(26): 15323-27, 1989.*
Townsend et al. "Immortalization and characterization of human cell lines with mast cell and monocytic properties" British Journal of Haematology 85: 452-461, 1993.*
Attoub, S. et al. "The c-kit Tyrosine Kinase Inhibitor STI571 for Colorectal Cancer Therapy" *Cancer Research*, Sep. 1, 2002, 62:4879-4883.
Auten, R.L. et al. "Nonpeptide CXCR2 Antagonist Prevents Neutrophil Accumulation in Hyperoxia-Exposed Newborn Rats" *The Journal of Pharmacology and Experimental Therapeutics*, 2001, 299(1):90-95.
Blank, U. et al. "The ins and outs of IgE-dependent mast-cell exocytosis" *TRENDS in Immunology*, May 2004, 25(5):266-273.
Burd, P.R. et al. "Interleukin 3-Dependent and -Independent Mast Cells Stimulated with IgE and Antigen Express Multiple Cytokines" *J. Exp. Med.*, Jul. 1989, 170:245-257.
Castellani, M.L. et al. "Expression and Secretion of CXCL8 (IL-8), Release of Tryptase and Transcription of Histidine Decarboxylase mRNA by Anti-IgE-Activated Human Umbilical Cord Blood-Derived Cultured Mast Cells" *NeuroImmunoModulation*, 2007, 14(2):97-104, Abstract.
Castellani, M.L. et al. "Immunological activation of human umbilical cord blood mast cells induces tryptase secretion and interleukin-6, and histidine decarboxilase mRNA gene expression" *Pharmacological Research*, 2007, 55:57-63.
Ditto, A.M. et al. "Use of the LAD-2 Mast Cell Line to Assess Mast Cell Degranulation Induced by Sera From Chronic Idiopathic Urticaria Patients" *J Allergy Clin Immunol*, Feb. 2006, 117(2):S120, Abstract.
Gilchrist, M. et al. "Expression, localization, and regulation of NOS In human mast cell lines: effects on leukotriene production" *Blood*, Jul. 15, 2004, 104(2):462-469.
Ho, K.K. et al. "Imidazolylpyrimidine based CXCR2 chemokine receptor antagonists" *Bioorg. Med. Chem. Lett.*, 2006, 16:2724-2728.

(Continued)

*Primary Examiner* — Robert Mondesi
*Assistant Examiner* — Emily A Cordas
(74) *Attorney, Agent, or Firm* — Saliwanchik, Lloyd & Eisenschenk

(57) ABSTRACT

The subject invention pertains to the development of a novel human mast cell line, USF-MC1. USF-MC1 is a mast cell precursor present in human umbilical cord blood (HUCB) that may be sustained in culture in the absence of exogenous cytokines to serve as a convenient experimental model of human mast cell activation. The SCF-independent human mast cell line USF-MC1 responds to IgE-mediated and IgE-independent stimuli in a way comparable to that of LAD2. USF-MC1 cells are useful for investigation of IgE-mediated activation mechanisms of human mast cells, contributing to the development of effective treatments for allergic disorders and other disorders. The subject invention provides a ready source of human mast cells for research, including pharmacological studies for the screening of various agents, and toxicologic, e.g., for the cosmetic and pharmaceutical industries. The mast cells can also be used as biofactories, for the large-scale production of biomolecules.

18 Claims, 16 Drawing Sheets

(56) References Cited

OTHER PUBLICATIONS

Irani, A.M. et al. "Recombinant Human Stem Cell Factor Stimulates Differentiation of Mast Cells From Dispersed Human Fetal Liver Cells" *Blood*, Dec. 15, 1992, 80(12):3009-3021.
Kempuraj, D. et al. "Characterization of Mast Cell-Committed Progenitors Present in Human Umbilical Cord Blood" *Blood*, May 15, 1999, 93(10):3338-3346.
Migliaccio, A.R. et al. "GATA-1 as a Regulator of Mast Cell Differentiation Revealed by the Phenotype of the GATA-1$^{low}$ Mouse Mutant" *J. Exp. Med.*, Feb. 3, 2003, 197(3):281-296.
Nakahata, T. et al. "Cytokines Regulate Development of Human Mast Cells from Hematopoietic Progenitors" *Int. J. Hematol.*, 2002, 75(4):350-356, Abstract.
Nilsson, G. et al. "C3a and C5a are Chemotaxins for Human Mast Cells and Act Through Distinct Receptors via a Pertussis Toxin-Sensitive Signal Transduction Pathway" *J. Immunol.*, 1996, 157:1693-1698.
Pompen, M. et al. "Airway epithelial cell mediators induce differentiation of an immature mast cell line" *Immunology Letters*, May 1997, 56(Part1):155.
Prussin, C. et al. "IgE, mast cells, basophils, and eosinophils" *J Allergy Clin Immunol*, Feb. 2003, 111(2):S486-S494.
Pulendran, B. et al. "A shot in the arm for mast cells" *Nature Medicine*, May 2008, 14(5):489-490.
Rivera, J. et al. "Molecular regulation of mast cell activation" *J Allergy Clin Immunol*, Jun. 2006, 117(6):1214-1225.
Salamon, P. et al. "Human mast cells release Interleukin-8 and induce neutrophil chemotaxis on contact with activated T cells" *Allergy*, 2005, 60:1316-1319.
Schulman, E.S. et al. "Human Lung Mast Cells: Purification and Characterization" *J. Immunol.*, Dec. 1982, 129(6):2662-2667.
Song, J.S. et al. "Tyrosine Phosphorylation of Vav Stimulates IL-6 Production in Mast Cells by a Rac/c-Jun N-Terminal Kinase-Dependent Pathway" *J. Immunol.*, 1999, 163:802-810.
Tagen, M. et al. "Mitochondrial Uncoupling Protein 2 Inhibits Mast Cell Activation and Reduces Histamine Content" *J. Immunol.*, 2009, 183:6313-6319.
Thangam, E.B. et al. "Airway smooth muscle cells enhance C3a-induced mast cell degranulation following cell-cell contact" *The FASEB Journal*, 2005, 19:778-800.
Turner, H. et al. "Signalling through the high-affinity IgE receptor FcεRl" Nature, Nov. 25, 1999, 402(Supp):B24-B30.
White, J.R. et al. "Identification of a Potent, Selective Non-peptide CXCR2 Antagonist That Inhibits Interleukin-8-induced Neutrophil Migration" *J. Biol. Chem.*, Apr. 24, 1998, 273(17):10095-10098.
Wisniewski, D. et al. "Characterization of Potent Inhibitors of the Bcr-Abl and the c-Kit Receptor Tyrosine Kinases" *Cancer Research*, Aug. 1, 2002, 62:4244-4255.
Bradfute, SB et al., "Roles of Sca-1 in hematopoietic stem/progenitor cell function" 2005, 33:836-843.
Delorme, B and Charbord, P, "Culture and Characterization of Human Bone Marrow Mesenchymal Stem Cells" *Methods in Molecular Medicine*, 2007, 140:67-81.
Gojo S et al., "In vivo cardiovasculogenesis by direct injection of isolated adult mesenchymal stem cells" *Experimental Cell Research*, 2003, 288:51-59.
Hattan, N. et al., "Purified cardiomyocytes from bone marrow mesenchymal stem cells produce stable intracardiac grafts in mice" *Cardiovascular Research*, 2005, 65:334-344.
Lu, Y et al., "Human Bone Marrow Mesenchymal Stem Cells Transfected with Human Insulin Genes Can Secrete Insulin Stably" *Annals of Clinical & Laboratory Science*, 2006, 36(2):127-136.
Nadri, S et al., "An efficient method for isolation of murine bone marrow mesenchymal stem cells" *International Journal of Developmental Biology*, 2007, 51:723-729.
Office Action dated Jan. 22, 2013 in U.S. Appl. No. 12/679,630, filed Jun. 28, 2010.
Office Action dated Sep. 6, 2013 in U.S. Appl. No. 12/679,630, filed Jun. 28, 2010.
Wang X et al., "The Role of Sca-1$^+$/CD31$^-$ Cardiac Progenitor Cell Population in Postinfarction Left Ventricular Remodeling" 2006, *Stem Cells*, 24:1779-1788.
Zahabi, A et al., "Expression of Constitutively Active Guanylate Cyclase in Cardiomyocytes Inhibits the Hypertrophic Effects of Isoproternol and Aortic Constriction on Mouse Hearts" *The Journal of Biological Chemistry*, 2003, 278(48):47694-47699.

* cited by examiner

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: LT primer (forward)

<400> SEQUENCE: 1
tagattccaa cctatggaac tat                                              23

<210> SEQ ID NO 2
<211> LENGTH: 24
<212> TYPE: DNA
<213> ORGANISM: Artificial Sequence
<220> FEATURE:
<223> OTHER INFORMATION: LT primer (reverse)

<400> SEQUENCE: 2
ggaaagtcct tggggtcttc tacc                                             24

<210> SEQ ID NO 3
<211> LENGTH: 24
<212> TYPE: DNA
<213> ORGANISM: Artificial Sequence
<220> FEATURE:
<223> OTHER INFORMATION: sense primer for IL-10

<400> SEQUENCE: 3
```

```
gctggaggac tttaagggtt acct                                          24
```

```
<210> SEQ ID NO 4
<211> LENGTH: 23
<212> TYPE: DNA
<213> ORGANISM: Artificial Sequence
<220> FEATURE:
<223> OTHER INFORMATION: antisense primer for IL-10

<400> SEQUENCE: 4
cttgatgtct gggtcttggt tct                                           23
```

```
<210> SEQ ID NO 5
<211> LENGTH: 19
<212> TYPE: DNA
<213> ORGANISM: Artificial Sequence
<220> FEATURE:
<223> OTHER INFORMATION: sense primer for IL-12 receptor beta 2

<400> SEQUENCE: 5
tccgacccaa agcccgaaa                                                19
```

```
<210> SEQ ID NO 6
<211> LENGTH: 22
<212> TYPE: DNA
<213> ORGANISM: Artificial Sequence
<220> FEATURE:
<223> OTHER INFORMATION: antisense primer for IL-12 receptor beta 2

<400> SEQUENCE: 6
ttccagagag tcagcgagag gt                                            22
```

```
<210> SEQ ID NO 7
<211> LENGTH: 23
<212> TYPE: DNA
<213> ORGANISM: Artificial Sequence
<220> FEATURE:
<223> OTHER INFORMATION: sense primer for TSLP

<400> SEQUENCE: 7
tatgagtggg accaaaagta ccg                                           23
```

```
<210> SEQ ID NO 8
<211> LENGTH: 22
<212> TYPE: DNA
<213> ORGANISM: Artificial Sequence
<220> FEATURE:
<223> OTHER INFORMATION: antisense primer for TSLP

<400> SEQUENCE: 8
gggattgaag gttaggctct gg                                            22
```

```
<210> SEQ ID NO 9
<211> LENGTH: 24
<212> TYPE: DNA
<213> ORGANISM: Artificial Sequence
<220> FEATURE:
<223> OTHER INFORMATION: sense primer for TNFSF4

<400> SEQUENCE: 9
cctggaagag aatgtgggaa atgc                                          24
```

```
<210> SEQ ID NO 10
<211> LENGTH: 24
<212> TYPE: DNA
```

```
<213> ORGANISM: Artificial Sequence
<220> FEATURE:
<223> OTHER INFORMATION: antisense primer for TNFSF4

<400> SEQUENCE: 10
ccgatgtgat acctgaagag caga                                          24

<210> SEQ ID NO 11
<211> LENGTH: 20
<212> TYPE: DNA
<213> ORGANISM: Artificial Sequence
<220> FEATURE:
<223> OTHER INFORMATION: sense primer for IL-17

<400> SEQUENCE: 11
agtgtaggaa cttgggctgc                                               20

<210> SEQ ID NO 12
<211> LENGTH: 22
<212> TYPE: DNA
<213> ORGANISM: Artificial Sequence
<220> FEATURE:
<223> OTHER INFORMATION: antisense primer for IL-17

<400> SEQUENCE: 12
agggtctctt gctggatggg aa                                            22
```

HUMAN MAST CELL LINE AND USES THEREOF

CROSS-REFERENCE TO RELATED APPLICATIONS

This application is the U.S. national stage application of International Patent Application No. PCT/US2010/027220, filed Mar. 12, 2010, which claims the benefit of U.S. Provisional Patent Application Ser. No. 61/210,046, filed Mar. 12, 2009, the disclosures of which are hereby incorporated by reference in their entireties, including all tables, figures, and amino acid and nucleic acid sequences.

BACKGROUND OF THE INVENTION

Mast cells are well-recognized for their role in innate and acquired immunity. Activation of mast cells by allergens and other stimuli leads to the release and de novo generation of a variety of airway inflammatory mediators including histamine, cysteinyl leukotrienes, prostaglandins, cytokines and enzymes such as tryptase. In asthma, mast cell-derived products can affect significant changes in airway architecture due to the close anatomical proximity of mast cells within the bronchial walls and adjacent blood vessels. Mast cell mediator release results in immediate bronchoconstriction as well as recruitment of other inflammatory cell types responsible for chronic airway inflammation that may ultimately lead to irreversible airway remodeling.

Study of human mast cell activation is limited by availability of few mast cell lines and their need for exogenous recombinant cytokines. Until 7 years ago, the only human cell culture available to researchers for study of mast cell biology was "human mast cell leukemia cells" termed HMC-1. One key limitation of HMC-1 is inconsistent ability to degranulate likely secondary to variable expression of the FceR1 alpha subunit. More recently, a second human mast cell line (LAD2) was described that more closely resembles characteristics of fully differentiated mature mast cells. LAD2 possesses the ability to consistently degranulate in response to IgE-mediated stimuli, as it expresses a complete FceR1 on its surface. Although LAD 2 represents a dramatic improvement over HMC-1 as a research tool to study mast cell biology, limitations include the requirement of costly exogenous cytokines to maintain the culture, and a neoplastic phenotype as the cells originated from a patient with mast cell sarcoma.

BRIEF SUMMARY OF THE INVENTION

Hematopoetic CD34+ stem cells differentiate toward a mast cell lineage in the bone marrow, then mast cell precursors migrate to circulation before realizing full maturation in end organ tissue. The inventors hypothesized that partially differentiated mast cell precursors exist and they are sustainable in the absence of high concentrations of exogenous cytokines. The inventors have discovered a mast cell precursor present in human umbilical cord blood (HUCB) that may be sustained in culture in the absence of exogenous cytokines to serve as a convenient experimental model of human mast cell activation.

One aspect of the invention concerns an isolated human mast cell obtainable from human HUCB. In some embodiments, the mast cell has one or more of the following characteristics: expresses the FceR1 receptor on its surface, expresses CD117 on its surface, expresses typtase, expresses chimase, and releases histamine.

Another aspect of the invention concerns a composition comprising isolated human mast cells of the invention.

Another aspect of the invention concerns a composition comprising at least partially purified human mast cells of the invention.

Another aspect of the invention pertains to a method for obtaining human mast cells, comprising separating hematopoietic stem cells from human umbilical cord blood, culturing the stem cells for a period of time, and, optionally, establishing single cell cultures from the cultured stem cells. In some embodiments, the stem cells are cultured in the presence of human stem cell factor (SCF), IL-6, and IL-3 for a period of time. In some embodiments, the single cell cultures are established using culture medium and 2% fetal bovine serum. Optionally, the method further comprises assessing whether the surviving colonies express both FcdR1 and CD117. In some embodiments, the method further comprises verifying that the mast cells express one or more markers that are characteristic of a human mast cell phenotype, such as tryptase expression, histamine release, IgE-induced cytokine expression, and non-immunologic stimuli-induced cytokine expression.

Another aspect of the invention concerns a method for determining pharmacological and biochemical activities of human mast cells of the invention, comprising assessing pharmacological and biochemical activities of human mast cell in vitro, wherein the human mast cells are obtained from human umbilical cord blood. Preferably, the human mast cells are at least partially purified from human umbilical cord blood.

Methods for assessing pharmacological and biochemical activities of human mast cells, such as mast cell degranulation, in response to one or more stimuli or conditions (e.g., candidate agents) are known in the art, and may be utilized in assessing such activities in the human mast cell of the invention (see Ditto A. et al., *Journal of Allergy and Clinical Immunology*, 2006, 117(2):S120-S120; Gilchrist M. et al., *Blood*, July 2004 (online Mar. 25, 2004), 104(2):462-469; Tagenn M. et al., *Journal of Immunology*, 2009, 183:6313-6319; Salamon P. et al., *Allergy*, 2005, 60(10):1316-1319; Shaoheng H. et al., *Allergy Methods and Protocols*, in Methods in Molecular Medicine, December 2007, 138:319-330; Nilsson G. et al., *Journal of Immunology*, 1996, 157(4):1693-1698; and Thangam E. B. et al., *The FASEB Journal*, 2005, 19:798-800, each of which are incorporated herein in its entirety).

Biological responses by mast cells of the invention to exposure to various stimuli, e.g., candidate agents, can be determined. The candidate agent can be a biological or non-biological agent. Mast cell response to stimuli can be assessed in a purified or partially purified state. In some embodiments, the mast cell response to stimuli is assessed in cell culture.

In some embodiments, the method for determining pharmacological and biochemical activities of human mast cells of the invention may comprise a method for identifying modulators of human mast cell survival, proliferation, function or phenotypic expression, comprising: (a) determining survival, proliferation, function or phenotypic expression of human mast cells of the invention in the presence of a potential modulator, wherein the human mast cells are obtained from human umbilical cord blood (and preferably partially or fully purified there from); and (b) comparing the determined survival, proliferation, function or phenotypic expression to the human mast cells in the absence of the potential modulator, wherein the modulator is identified by an increase or decrease in survival, proliferation, function or phenotypic expression of the human mast cells in its presence.

In some embodiments, the modulator to be identified is a mast cell stabilizer. Mast cell stabilizers inhibit or reduce mast cell degranulation, stabilizing the cells and thereby preventing or reducing the release of histamine and related mediators. Thus, potential mast cell stabilizers can be identified in accordance with the invention by contacting a mast cell or composition of the invention with a candidate agent, and determining whether the agent inhibits or reduces mast cell degranulation. Preferably, the determination is made relative to an appropriate experimental control. In some embodiments, the candidate agent is a small organic or inorganic molecule, a polypeptide (a chain of amino acids of any length, e.g., a protein or peptide), a pharmacologic agent, or a biological compound. Identified modulators may be useful in the prevention and/or treatment of diseases involving abnormal human mast cell function.

As the mast cells of the invention may be used as a model of human mast cell activation, another aspect of the invention comprises a method for identifying (screening for) agents that modulate activation of mast cells, comprising contacting a human mast cell obtainable from human umbilical cord blood with a candidate agent, and determining whether the candidate agent modulates activation of the cell. In some embodiments, the screening method comprises determining whether the candidate agent induces or increases activation of the mast cell. In some embodiments, the method comprises determining whether the candidate agent inhibits activation of the mast cell.

In some embodiments, the method for determining pharmacological and biochemical activities of human mast cells of the invention may comprise a method for identifying modulators of human mast cell migration, comprising: (a) determining migration of human mast cells of the invention in the presence of a potential migration modulator, wherein the human mast cells are obtained from human umbilical cord blood (and preferably partially or fully purified there from); and (b) comparing the migration of the mast cells to migration of the cells in the absence of the potential modulator, wherein the modulator is identified by an increase or decrease in migration of the human mast cells in its presence.

In some embodiments, the method for determining pharmacological and biochemical activities of human mast cells of the invention may comprise a method for identifying modulators of human mast cell proliferation, comprising: (a) deter mining proliferation of human mast cells of the invention in the presence of a potential proliferation modulator, wherein the human mast cells are obtained from human umbilical cord blood (and preferably partially or fully purified there from); and (b) comparing the proliferation of the mast cells to proliferation of the cells in the absence of the potential modulator, wherein the modulator is identified by an increase or decrease in proliferation of the human mast cells in its presence. Modulators that reduce the numbers of mast cells or reduce mast cell activity (e.g., reduce mast cell activity) may potentially be useful as agents for treating mast cell disease (mastocytosis), a disease characterized by the presence of too many mast cells in various organs and tissues.

Another aspect of the invention concerns a cell transplantation method. In this aspect of the invention, the method is a method for transplanting an effective amount of human mast cells of the invention to a human or non-human mammal, wherein the mast cells are obtained from human umbilical cord blood. The cells can be administered locally at a desired anatomical site or systemically. In some embodiments, the cells are administered intravenously. The cells can be administered to the mammal to treat a mast cell disorder or a disorder characterized by loss, damage, or dysfunction of mast cells, e.g., as mast cell replacement therapy. The cells can also be administered to a non-human mammal, such as an animal model of disease, for research purposes. Preferably, the mast cells administered to the mammal are at least partially purified. In some embodiments, the mast cells are isolated from the human umbilical cord blood.

BRIEF DESCRIPTION OF THE DRAWINGS

FIG. 1A is a scatter plot of human cord blood stem cells cultured for 8 weeks in the presence (lower panel) or absence (upper panel) of SCF and IL-6. The upper panel shows stem cells cultured in the absence of SCF and IL-6 demonstrate staining only for CD117. The lower panel shows stem cells cultured in the presence of SCF and IL-6 demonstrate double staining for the IgE receptor, FceR1 and CD117 (cKIT). FIG. 1B shows flow cytometry of single cell-derived USF-MC1 cells cultured for 12 weeks in the absence of SCF and IL-6. Despite the absence of SCF and IL-6 for 12 weeks, USF-MC1 cells stain positively for FceR1 and CD117.

FIG. 4A shows mRNA expression in LAD2 cells and USF-MC1 cells (top and bottom, respectively). FIG. 4B shows IL-10 mRNA expression in LAD2 cells and USF-MC1 cells (top and bottom, respectively). FIG. 4C shows mRNA expression of TNFSF4 in LAD2 cells and USF-MC1 cells (left and right, respectively). FIG. 4D shows LAD2 and USF-MC1 mRNA expression of IL-17 in LAD2 cells and USF-MC1 cells (left and right, respectively).

FIG. 5A shows flow cytometry showing double staining of USF-MC1 SV40 LT cells with CD 117 and FceR1. FIG. 5B shows cellular staining of USF-MC1 SV40 LT cells with DAPI (top panel), chymase (middle panel), and tryptase (bottom panel). FIG. 5C shows histamine (beta-hexosaminidase) release from USF-MC1 SV40 LT transfected cells and non-transfected USF-MC1 cells; Percent beta-hexosaminidase release 30 minutes following IgE-mediated challenge.

BRIEF DESCRIPTION OF THE SEQUENCES

Figure 1A:
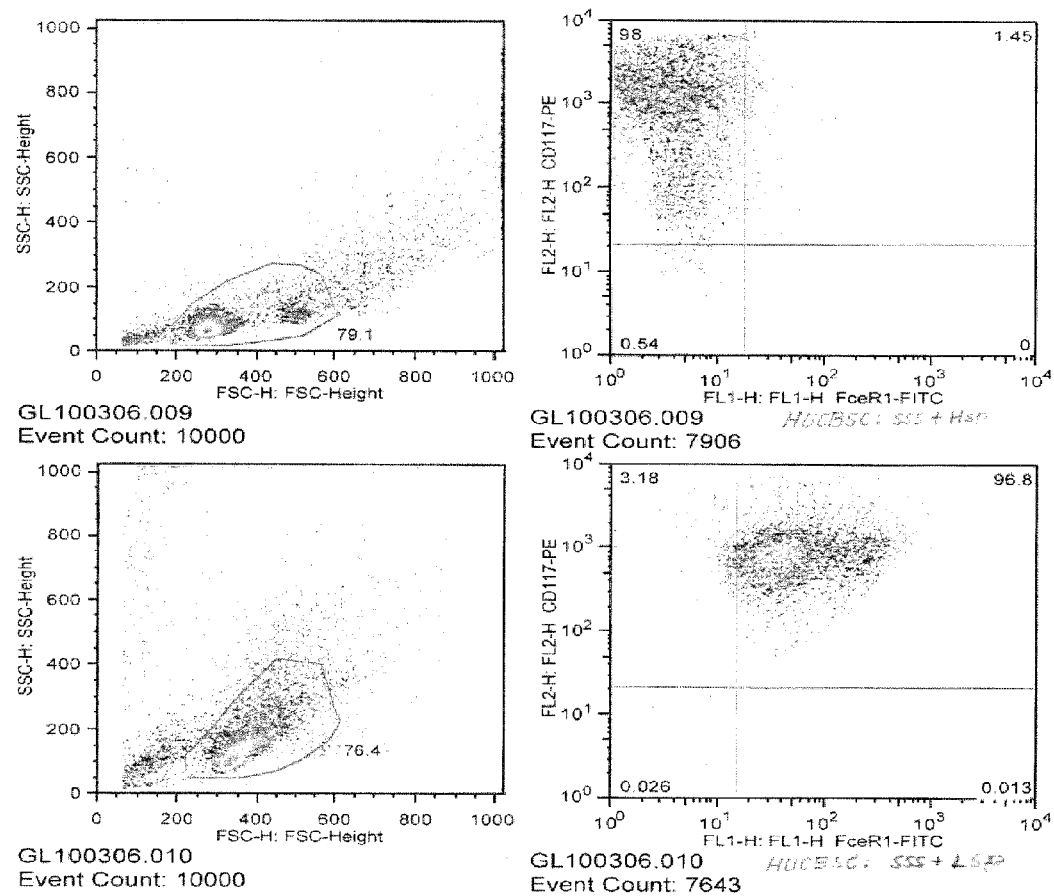
FIGS. 1A-1B show flow cytometry scatter plots.
Figure 1B:
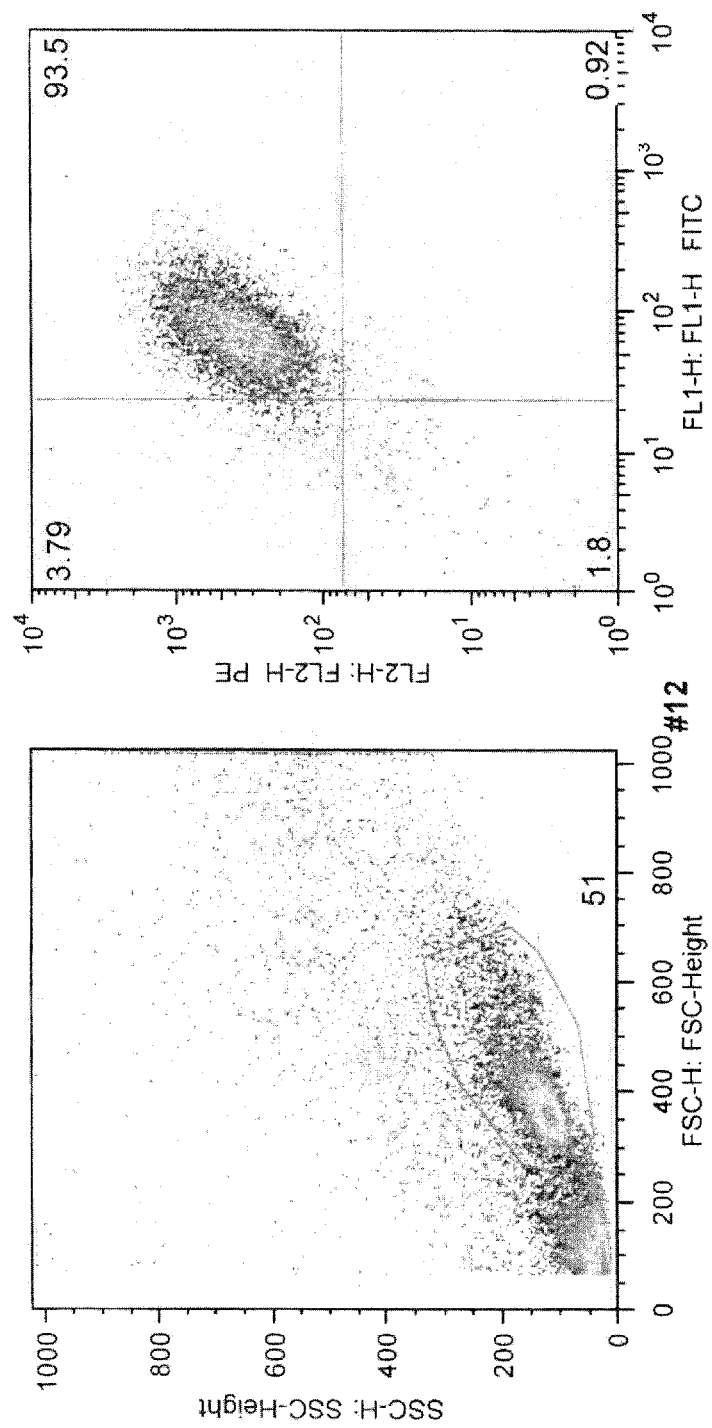

SEQ ID NO: 1 is an LT primer (forward).
SEQ ID NO: 2 is an LT primer (reverse).
SEQ ID NO: 3 is a sense primer for interleukin-10 (IL-10) (see Table 1).

SEQ ID NO: 4 is an antisense primer for IL-10 (see Table 1).

SEQ ID NO: 5 is a sense primer for interleukin-12 (IL-12) receptor beta 2 (see Table 1).

SEQ ID NO: 6 is an antisense primer for IL-12 receptor beta 2 (see Table 1).

SEQ ID NO: 7 is a sense primer for TSLP (see Table 1).

SEQ ID NO: 8 is an antisense primer for TSLP (see Table 1).

SEQ ID NO: 9 is a sense primer for TNFSF4 (see Table 1).

SEQ ID NO: 10 is an antisense primer for TNFSF4 (see Table 1).

SEQ ID NO: 11 is a sense primer for interleukin-17 (IL-17) (see Table 1).

SEQ ID NO: 12 is an antisense primer for IL-17 (see Table 1).

DETAILED DESCRIPTION

The subject invention pertains to the development of a novel human mast cell line. Mast cells initiate allergic inflammation through IgE-mediated release of pre-formed mediators, leukotrienes and cytokines. Study of human mast cell activation is limited by availability of few mast cell lines and their need for exogenous recombinant cytokines. The inventors have discovered a mast cell precursor present in human umbilical cord blood (HUCB) that may be sustained in culture in the absence of exogenous cytokines, and that may serve as a convenient experimental model of human mast cell activation.

Stem cells were isolated from HUCB using CD133 bead selection. Purified cells were cultured in human stem cell factor (SCF), IL-6 and IL-3 for 14 days. After continued culture in SCF and IL-6, single cell cultures were established in 96-well plates using only culture medium and 2% fetal bovine serum (FBS). Of 10 surviving colonies, one expressed both FceR1 and CD117 on its surface by flow cytometry. Immunocytochemistry revealed uniform expression of tryptase with 30% chymase staining. In both USF-MC1 and the established human mast cell line LAD2, IgE cross-linking, ionomycin, and ANP-challenge induced 30 to 50% B-Flex release at 1 hr and 5-15 fold increase in LTC4 release at 6 hr. ANP-induced release of both B-Hex and LTC4 was reduced to baseline by isatin, an ANP receptor antagonist. Cytokine expression was induced by IgE and non-immunologic stimuli in a similar fashion in both LAD2 and USF-MC1. USF-MC1 was successfully transfected with SV40 LT with retained expression of tryptase, chymase, FceR1 CD117 and ability to release histamine. These findings show that SCF-independent mast cell precursors exist in HUCB. The SCF-independent human mast cell line USF-MC1 responds to IgE-mediated and IgE-independent stimuli in a way comparable to that of LAD2.

One aspect of the invention concerns an isolated human mast cell obtainable from human HUCB. In some embodiments, the mast cell has one or more of the following characteristics: expresses the FceR1 receptor on its surface, expresses CD117 on its surface, expresses typtase, expresses chimase, and releases histamine.

Another aspect of the invention concerns a composition comprising isolated human mast cells of the invention.

Another aspect of the invention concerns a composition comprising at least partially purified or enriched human mast cells of the invention. In some embodiments, the composition further comprises a pharmaceutically acceptable carrier. In some embodiments, the composition is a cell culture comprising at least partially purified or enriched human mast cells of the invention and a culture medium.

Another aspect of the invention pertains to a method for obtaining human mast cells, comprising separating hematopoietic stem cells from human umbilical cord blood, and culturing the stem cells for a period of time. In some embodiments, the stem cells are cultured in the presence of human stem cell factor (SCF), IL-6, and IL-3 for a period of time (e.g., such as 7-14 days or more). After the stem cells are cultured, single cell cultures can be established (e.g., in multi-well plates). In some embodiments, the single cell cultures are established using culture medium and 2% fetal bovine serum. Surviving colonies can then be examined for expression of mast cell-specific phenotypic markers. For example, the method can further comprise assessing whether the surviving colonies express FcdR1 and/or CD117. In some embodiments, the method further comprises verifying that the mast cells express one or more markers that are characteristic of a human mast cell phenotype, such as tryptase expression, histamine release, IgE-induced cytokine expression, and non-immunologic stimuli-induced cytokine expression.

Preferably, the hematopoietic stem cells separated from the human umbilical cord blood are CD133+. In some embodiments, the stem cells are CD133+ and the stem cells are separated on the basis of CD133 positivity. Various other techniques may be utilized to separate or purify the hematopoietic stem cells from human umbilical cord blood, including those disclosed in Stem Cells: Scientific Progress and Future Research Directions, Appendix E1-E5 and throughout, report prepared by the National Institutes of Health, June, 2001, which is incorporated herein by reference in its entirety.

Another aspect of the invention concerns a method for determining pharmacological and biochemical activities of human mast cells of the invention, comprising assessing pharmacological and biochemical activities of human mast cell in vitro, wherein the human mast cells are obtained from human umbilical cord blood. Preferably, the human mast cells are at least partially purified from human umbilical cord blood.

Methods for assessing pharmacological and biochemical activities of human mast cells, such as mast cell degranulation, in response to one or more stimuli or conditions (e.g., candidate agents) are known in the art, and may be utilized in assessing such activities in the human mast cell of the invention (see Ditto A. et al., *Journal of Allergy and Clinical Immunology*, 2006, 117(2):S120-S120; Gilchrist M. et al., *Blood*, July 2004 (online Mar. 25, 2004), 104(2):462-469; Tagenn M. et al., *Journal of Immunology*, 2009, 183:6313-6319; Salamon P. et al., *Allergy*,2005, 60(10):1316-1319; Shaoheng H. et al., *Allergy Methods and Protocols*, in Methods in Molecular Medicine, December 2007, 138:319-330; Nilsson G. et al., *Journal of Immunology*, 1996, 157(4):1693-1698; and Thangam E. B. et al., *The FASEB Journal*, 2005, 19:798-800, each of which are incorporated herein in its entirety).

Biological responses by mast cells of the invention to exposure to various candidate agents can be determined. Mast cell response to stimuli can be assessed in a purified or partially purified state. In some embodiments, the mast cell response to stimuli is assessed in cell culture. Examples of candidate agents include polypeptides (e.g., a protein, peptide, antibody), cells, tissues, nucleic acid molecules, and small molecules. Without limitation, a candidate agent can be a known compound or a novel compound to be developed in the future. It may be a low-molecular-weight compound or a high-molecular-weight compound. In this context, the low-molecular-weight compound is a compound having a molecular weight of less than approximately 3000, which includes, for example, an organic compound and a derivative thereof and an inorganic compound usually available as a pharmaceutical agent, and refers to a compound and a derivative thereof produced by making full use of organic synthesis or the like, a naturally occurring compound and a derivative thereof, small nucleic acid molecules such as promoter, a variety of metals and the like, and desirably an organic compound and a derivative thereof and a nucleic acid molecule available as a pharmaceutical agent. The high-molecular-weight compound is a compound having a molecular weight of not lower than approximately 3000, which includes, for example, polypeptide (chain of amino acids of any length), nucleic acid, polysaccharide and combinations thereof. These low-molecular-weight or high-molecular-weight compounds, if they are known, are commercially available or can be obtained by way of steps such as collection, production and purification according to the respective reported documents. These compounds may be naturally occurring or prepared by genetic engineering, or can also be obtained by semi-synthesis and the like.

The candidate agent can be a biological or non-biological agent. The term "biological agent" refers to any agent of biological origin, such as a virus, protein, peptide, amino acid, lipid, carbohydrate, nucleic acid, nucleotide, drug, pro-drug, or other substance that may have an effect on mast cells, whether such effect is harmful, beneficial, or otherwise.

The effects candidate agents on the cells can be identified on the basis of significant difference relative to control cultures with respect to criteria such as the ratios of expressed phenotypes, cell viability and alterations in gene expression. Physical characteristics of the cells can be analyzed by observing cell morphology and growth with microscopy. Increased or decreased levels of proteins, such as enzymes, receptors and other cell surface molecules, amino acids, peptides, and biogenic amines can be analyzed with any technique known in the art which can identify the alteration of the level of such molecules. These techniques include immunohistochemistry, using antibodies against such molecules, or biochemical analysis. Such biochemical analysis includes protein assays, enzymatic assays, receptor binding assays, enzyme-linked immunosorbent assays (ELISA), electrophoretic analysis, analysis with high performance liquid chromatography (HPLC), Western blots, and radioimmune assays (RIA). Nucleic acid analysis, such as Northern blots and polymerase chain reaction (PCR) can be used to examine the levels of mRNA coding for these molecules, or for enzymes which synthesize these molecules.

Optionally, mast cells treated with candidate agents can be transplanted into an animal, and their survival and biochemical and immunological characteristics examined as previously described.

In some embodiments, the method for determining pharmacological and biochemical activities of human mast cells of the invention may comprise a method for identifying modulators of human mast cell survival, proliferation, function or phenotypic expression, comprising: (a) determining survival, proliferation, function or phenotypic expression of human mast cells of the invention in the presence of a potential modulator, wherein the human mast cells are obtained from human umbilical cord blood (and preferably partially or fully purified there from); and (b) comparing the determined survival, proliferation, function or phenotypic expression to the human mast cells in the absence of the potential modulator, wherein the modulator is identified by an increase or decrease in survival, proliferation, function or phenotypic expression of the human mast cells in its presence.

In some embodiments, the modulator to be identified is a mast cell stabilizer. Mast cell stabilizers inhibit or reduce mast cell degranulation, stabilizing the cells and thereby preventing or reducing the release of histamine and related mediators. Thus, potential mast cell stabilizers can be identified in accordance with the invention by contacting a mast cell or composition of the invention with a candidate agent, and determining whether the agent inhibits or reduces mast cell degranulation. Preferably, the determination is made relative to an appropriate experimental control. In some embodiments, the candidate agent is a small organic or inorganic molecule, a polypeptide (a chain of amino acids of any length, e.g., a protein or peptide), a pharmacologic agent, or a biological compound. Identified modulators may be useful in the prevention and/or treatment of diseases involving abnormal human mast cell function.

Mast cells contain many granules rich in histamine and heparin, and are often identified by their staining characteristics and large granules. Although they are best known for their role in allergy, anaphylaxis, and asthma, mast cells play an important protective role as well, being intimately involved in wound healing and defense against pathogens. Mast cells play a role in the inflammatory process. When activated, a mast cell rapidly releases the contents of its granules (degranulation) and various hormonal mediators into the interstitium. Mast cells can be stimulated to degranulate by direct injury (e.g., physical or chemical), cross-linking to immunoglobulin E (IgE) receptors, or by activated complement proteins.

Activation of mast cells induces the release of preformed inflammatory mediators localized in specialized granules and the de novo synthesis and secretion of cytokines, chemokines, and eicosanoids. In allergic reactions, for example, mast cells remain inactive until an allergen binds to IgE that is in association with the cell. Other membrane activation events can either prime mast cells for subsequent degranulation or can act in synergy with FceRI signal transduction (Pulendran B. and Ono S. J., *Nat. Med.*, May 2008, 14(5): 489-90, which is incorporated herein by reference in its entirety). Allergens, which are typically proteins or polysaccharides or have such components, bind to the antigen-binding sites, which are situated on the variable regions of the IgE molecules bound to the mast cell surface. Binding of two or more IgE molecules (cross-linking) may be required to activate the mast cell. The clustering of the intracellular domains of the cell-bound Fc receptors, which are associated with the cross-linked IgE molecules, causes a sequence of reactions inside the mast cell that lead to its activation.

Molecules released into the extracellular environment upon activation by mast cells can include preformed mediators (from mast cell granules), e.g., histamine, serotonin, proteoglycans such as heparin, serine proteases such as typtase; newly formed lipid mediators (eicosanoids) such as prostaglandin D2, leukotriene c4, and platelet-activating factor; and cytokines such as eosinophil chemotactic factor (Prussin C. and Metcalfe D. D., *J Allergy Clin Immunol.*, 2003, 111(2 Suppl): S486-94, which is incorporated herein by reference in its entirety).

The presence of one or more of these molecules, or changes in the amounts of one or more of these molecules, may be used as a marker (indicator) of mast cell activation. Methods for detecting such molecules are known in the art and may be utilized to detect modulation of mast cell activation.

As the mast cells of the invention may be used as a model of human mast cell activation, another aspect of the invention comprises a method for identifying (screening for) agents that modulate activation of mast cells, comprising contacting a human mast cell obtainable from human umbilical cord blood with a candidate agent, and determining whether the candidate agent modulates activation of the cell. In some embodiments, the screening method comprises determining whether the candidate agent induces or increases activation of the mast cell. In some embodiments, the method comprises determining whether the candidate agent inhibits activation of the mast cell. Methods for detecting mast cell activation and modulation of mast cell activation are known in the art (see, for example, Rivera J. and Gilfillan A. M., *J. Allergy Clin. Immunol.*, 2006, 117(6):1214-1225, which is incorporated herein by reference in its entirety). Candidate agents can be, for example, polypeptides (e.g., a protein, peptide, antibody), cells, tissues, nucleic acid molecules, or small molecules. A specific example of such a modulator is a monoclonal antibody that is capable of binding to IgE and will inhibit binding of IgE to the mast cell high-affinity FcE receptor, such as that disclosed in U.S. Pat. No. 4,940,782 (Rup et al.).

In some embodiments, the method for determining pharmacological and biochemical activities of human mast cells of the invention may comprise a method for identifying modulators of human mast cell migration, comprising: (a) determining migration of human mast cells of the invention in the presence of a potential migration modulator, wherein the human mast cells are obtained from human umbilical cord blood (and preferably partially or fully purified there from); and (b) comparing the migration of the mast cells to migration of the cells in the absence of the potential modulator, wherein the modulator is identified by an increase or decrease in migration of the human mast cells in its presence.

In some embodiments, the method for determining pharmacological and biochemical activities of human mast cells of the invention may comprise a method for identifying modulators of human mast cell proliferation, comprising: (a) determining proliferation of human mast cells of the invention in the presence of a potential proliferation modulator, wherein the human mast cells are obtained from human umbilical cord blood (and preferably partially or fully purified there from); and (b) comparing the proliferation of the mast cells to proliferation of the cells in the absence of the potential modulator, wherein the modulator is identified by an increase or decrease in proliferation of the human mast cells in its presence. Modulators that reduce the numbers of mast cells or reduce mast cell activity (e.g., reduce mast cell activity) may potentially be useful as agents for treating mast cell disease (mastocytosis), a disease characterized by the presence of too many mast cells in various organs and tissues.

Several compounds are known to inhibit mast cell proliferation and/or migration, such as antihistamines, CXCR antagonists, and C-kit inhibitors. Histamine acts as an autocrine and paracrine mediator and as a chemo-attractant for mast cells, acting through the $H_4$ receptor on mast cells. Histamine is released from mast cells in response to $H_1$ receptor activation on mast cells. Therefore, antihistamines inhibit mast cell proliferation and migration. Antihistamines include compounds that selectively or nonselectively inhibit histamine receptors, and include azelastine, oxatomide, terfenadine, epinastine and astemizole, diphenhydramine, loratadine, desloratadine, meclizine, quetiapine, fexofenadine, cimetidine, famotidine, ranitidine, ABT-239, cipralisant, ciproxifan, clobenpropit, thioperamide and/or agents that selectively inhibit (e.g., selectively inhibit) a histamine receptor, including $H_4$ and $H_1$ receptors.

CXC chemokine receptors are integral membrane proteins that specifically bind and respond to cytokines of the CXC chemokine family. They represent one subfamily of chemokine receptors, a large family of seven transmembrane G protein-linked receptors. There are several known CXC chemokine receptors in mammals, including CXCR1 through CXCR7. CXCR1 and CXCR2 (also known as IL8RB; CD182; IL8RA; CDw128b; CMKAR2; IL8R2) are expressed on surface of mast cells. Mast cells migrate and are precursors recruited by CXC chemokines with the ELR tripeptide motif, such as IL-8, GRO-a, NAP-2, and ENA-78. CXCR2 antagonists are known in the art. Some non-limiting examples include: SB 225002 (*J. Biol. Chem.*, Apr. 24, 1998, 273(17):10095-10098); SB 265610 (*JPET,* 2001, 299:90-95) certain nicotinamide N-oxides; certain Phenol-containing antagonists of the CXCR2 receptor; and certain imidazolylpyrimidines (*Bioorg Med Chem. Lett.* 2006 May 15; 16(10):2724-8).

The c-kit proto-oncogene encodes a transmembrane tyrosine kinase receptor. Activation of c-kit by stem cell factor (SCF, also called kit ligand) its natural ligand, promotes its dimerization and autophosphorylation at specific tyrosine residues Tyr567 and Tyr719. Signaling by c-kit plays an important role in cellular transformation and differentiation, including proliferation, survival, adhesion, and chemotaxis of several cell types (including mast cells). Agents that inhibit the activation of c-kit are "c-kit inhibitors" and are known in the art, and include imatinib; 2-phenylaminopyrimidine derivative ST1571 (available from Novartis; see, Attoub et al., *Cancer Research, September* 2002, 62, 4879-4883); compounds disclosed in Wisniewski D, *Cancer Res., August* 2002, 62(15):4244-55 including PD173955 and PD180970; and compounds disclosed in Published PCT application WO/2003/002114.

Another aspect of the invention concerns a cell transplantation method. In this aspect of the invention, the method is a method for transplanting an effective amount of human mast cells of the invention to a human or non-human mammal, wherein the mast cells are obtained from human umbilical cord blood. The cells can be administered locally at a desired anatomical site or systemically. In some embodiments, the cells are administered intravenously. The cells can be administered to the mammal to treat a mast cell disorder or a disorder characterized by loss, damage, or dysfunction of mast cells, e.g., as mast cell replacement therapy. The cells can also be administered to a non-human mammal, such as an animal model of disease, for research purposes. Preferably, the mast cells administered to the mammal are at least partially purified. In some embodiments, the mast cells are isolated from the human umbilical cord blood.

In accordance with methods of the invention, one or more proliferative, phenotypic and functional characteristics of human mast cells and compositions (e.g., cell cultures) of the present invention can be assessed under various conditions and in the presence of various stimuli, e.g., candidate agents. Proliferation of the human mast cells can be assessed, for example, by determining cell count in wells of a multiwall plate over a representative period of time (e.g., 4 to 8 weeks). Approximately one-half of the cells can then removed from each well. Cell counts are subsequently repeated (e.g., one week later) to determine if human mast cell numbers increased, decreased, or remained the same.

Uptake of $^3$H-thymidine can also monitored as a measure of survival and proliferation of human mast cell cultures of the present invention in the presence of different potential stimuli, such as cytokine growth factors. In this procedure, $^3$H-thymidine can be added to human mast cell aliquots from umbilical cord blood over time (for example, 5 through 7 weeks of culture). Survival and proliferation of human mast cells cultured in medium in the presence of an candidate agent can be compared to that of mast cells cultured in culture medium alone.

Uptake of BrdU can also monitored to assess cell division. At day 0, BrdU (e.g., 10 μM) is added to cultured human mast cells. Weekly, aliquots are removed for analyses. By 3-4 weeks of culture inception, relative amounts (percentages) of positively stained cells are noted.

Mast cell granules contain chemical mediators such as histamine and cytokines, and the degranulation reaction in mast cell plays an important role in allergic diseases such as pollinosis, bronchial asthma and atopic dermatitis, and various inflammatory diseases including autoimmune diseases. Therefore, suppression of the degranulation reaction can be effective as a treatment method of these diseases.

Agents that suppress the release of the chemical mediators due to the degranulation reaction by stabilizing the membrane of the mast cell include Intal (sodium cromoglycate), Rizaben (tranist) and the like, and they have been used as anti-allergic agents in clinical application. The degranulation is caused by signal transduction through the IgE receptor. Since this process depends on calcium ion, the control of the degranulation reaction has also been attempted by controlling the intracellular calcium concentration.

Conventional techniques for studying and assessing the degranulation reaction and the anti-allergic agents can be found, for example, in Turner H. & Kinet J P., *Nature*, 1999, 402:B24-30, and Blank U, Rivera J., *TRENDS in Immunology*, 2004, 25:266-273, which are incorporated herein by reference in their entirety. Conventional techniques regarding the cytokine production from mast cells can be found, for example, in Burd P. R. et al., *J. Exp. Med.*, 1989, 170:240-257, and Song J. S. et al., *J. Immunology*, 1999, 163:802-810, which are incorporated by reference herein in their entirety.

Histamine is a prominent preformed mediator of the mast cell. Therefore, release of histamine by mast cells of the invention in response to various stimuli can be examined. Cultured human mast cells of the present invention can be examined during culture over time for histamine content or release (see, for example, Schulman et al., *J. Immunol.*, 1982, 129:2662-67, which is incorporated herein by reference in its entirety). Histamine release in the presence of various stimuli can be compared to histamine release in the absence of the stimuli to assess the influence or effective of the stimuli on histamine release, e.g., modulation (increases or decreases) in histamine release.

Two receptors with differing affinities for IgE have been identified and characterized. The high affinity receptor (FceR1) is expressed on the surface of mast cells and basophils. The low affinity receptor (FceRII/CD23) is expressed on many cell types including B cells, T cells, macrophages, eosinophils and Langerhan cells. The high affinity IgE receptor includes three subunits (alpha, beta and gamma chains). Several studies demonstrate that only the alpha chain is involved in the binding of IgE, whereas the beta and gamma chains (which are either transmembrane or cytoplasmic proteins) are required for signal transduction events. The identification of IgE structures required for IgE to bind to the FceR1 on mast cells and basophils is of utmost importance in devising strategies for treatment or prevention of IgE-mediated allergies, such as the use of peptides or small molecules that block the binding of IgE to receptor-bearing cells in vivo. Thus, the mast cells of the invention can be used to screen compounds such as peptides and small molecules to identify agents that block the binding of IgE to FceR1.

The mast cells of the invention can be genetically modified with nucleic acids that are native (endogenous) or foreign (heterologous) to the cells. For examples, the cells may be genetically modified to produce proteins, peptides, hormones, growth factors, and other biologically active biomolecules. The mast cells of the invention can be genetically modified to modulate (e.g., inhibit expression, inactivate, or overexpress) endogenous genes, such as the high affinity IgE receptor (FceR1) or CD117 (C-Kit).

The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides.

Exogenous nucleic acids can be introduced into a mast cell of the invention by viral vectors (retrovirus, modified herpes virus, herpes virus, adenovirus, adeno-associated virus, and the like), non-viral vectors (e.g., lipid-based or liposomal delivery), or direct DNA transfection (calcium phosphate transfection, DEAE-dextran, electroporation, and the like), for example.

Differentiation of the mast cells of the invention can be influenced using methods known in the art. For example, mast cells can be induced to differentiate using techniques involving exposure to growth factors and contact with fibroblasts (see, for example, Kitamura Y. and Fujita J., *BioEssays*, February 2005, 10(6):193-196; Irani A. M. et al., *Blood*, 1992, 80(12):3009-3021; Pompen M. et al., *Immunology Letters*, May 1997, 56(Part 1):155; and Migliaccio A. R. et al., *Journal of Experimental Medicine*, February 2003, 197(3):281-296, which are each incorporated herein by reference in its entirety).

The mast cells of the invention can be used as a platform for growing bacteria, virus particles for vaccine production or other purposes, or other microorganisms. For example, mast cells have been demonstrated to be a potential reservoir of infection for several pathogens, such as HIV-1 and dengue virus, and capable of producing mediators following challenge with a number of viral products. Thus, the mast cells of the invention may be used to grow and study such microorganisms, and test potential treatments and prophylactic agents.

The mast cells of the subject invention can be administered to a human or non-human mammal in isolation or within a pharmaceutical composition comprising the mast cells and a pharmaceutically acceptable carrier. As used herein, a pharmaceutically acceptable carrier includes solvents, dispersion media, coatings, antibacterial and antifungal agents, isotonic agents, and the like. Pharmaceutical compositions can be formulated according to known methods for preparing pharmaceutically useful compositions. Formulations are described in a number of sources that are well known and readily available to those of ordinary skill in the art. For example, *Remington's Pharmaceutical Science* (Martin E. W., Easton Pa., Mack Publishing Company, 19$^{th}$ ed.) describes formulations that can be used in connection with the subject invention. Fat mulations suitable for parenteral administration, for example, include aqueous sterile injection solutions, which may contain antioxidants, buffers, bacteriostats, and solutes that render the formulation isotonic with the blood of the intended recipient; and aqueous and non-aqueous sterile suspensions that may include suspending agents and thickening agents. It should be understood that in addition to the ingredients particularly mentioned above, the formulations of the subject invention can include other agents conventional in the art having regard to the type of formulation and route of administration in question.

The mast cells of the subject invention (genetically modified or not genetically modified) can be administered on or within a variety of carriers that can be formulated as a solid, liquid, semi-solid, etc. For example, genetically modified cells or non-genetically modified cells can be suspended within an injectable hydrogel composition (U.S. Pat. No. 6,129,761) or encapsulated within microparticles (e.g., microcapsules) that are administered to the mammal and, optionally, released at the target anatomical site (Read T. A. et al., Nature Biotechnology, 2001, 19:29-34, 2001; Joki T. et al., Nature Biotechnology, 2001, 19:35-38; Bergers G. and Hanahan D., Nature Biotechnology, 2001, 19:20-21; Dove A. Nature Biotechnology, 2002, 20:339-343; Sarkis R. Cell Transplantation, 2001, 10:601-607).

In situations where the mammal is suffering from a disorder amenable to treatment with mast cells, the mast cells of the subject invention are preferably administered to the mammal in an amount effective to provide a therapeutic benefit. A "therapeutically effective amount" is that amount effective to treat the condition. For purposes of the subject invention, the terms "treat" or "treatment" include preventing, inhibiting, reducing the occurrence of and/or ameliorating the physiological effects of the pathological condition to be treated. Preferably, the cells are administered to the mammal in an amount within the range of about $10^4$ to about $10^{10}$ cells. More preferably, the cells are administered to the mammal in an amount within the range of about $10^7$ to about $10^{10}$ cells. Doses of cells can be determined by one of ordinary skill in the art, with consideration given to such factors as cell survival rate following administration, the number of cells necessary to induce a physiologic response in the normal state, and the species of the mammal.

The mast cells can be administered to a mammal by any method of delivery, such as intravascularly, intracranially, intracerebrally, intramuscularly, intradermally, intravenously, intraocularly, orally, nasally, topically, or by open surgical procedure, depending upon the anatomical site or sites to which the mast cells are to be delivered. The mast cells can be administered in an open manner, as in the heart during open heart surgery. The mast cells can be infused intravenously, for example. The mast cells can be co-administered with other cell types or biologically active agents such as drugs (e.g., immunosuppressive agents).

The mast cells of the invention can be administered as autografts, syngeneic grafts, allografts, and xenografts, for example. As used herein, the term "graft" refers to one or more cells intended for implantation within a human or other mammal. Hence, the graft can be a cellular or tissue graft, for example. In some embodiments, the cells are autologous (the recipient's own cells), i.e., administered as an autograft. The mast cells of the invention can be obtained from banked (e.g., frozen and stored) or unbanked umbilical cord blood. For example, the subject's umbilical cord blood can be harvested at birth and banked for later use. Mast cells of the invention can be isolated from the banked cord blood at a later date and utilized as necessary.

The practice of the present invention can employ, unless otherwise indicated, conventional techniques of molecular biology, microbiology, recombinant DNA technology, electrophysiology, and pharmacology, that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press)).

As used herein, the term "culture" is used to denote the maintenance or cultivation of cells in vitro including the culture of single cells. Cultures can be cell, tissue, or organ cultures, depending upon the extent of organization.

As used herein, the term "cell line" is used to refer to cells which have arisen from a primary culture and capable of successful subculture.

As used herein, the term "isolated" means removal from its native environment, and can include removal from its immediate native environment. As used herein, the term "isolated mast cell" or "isolated mast cells" indicates that the cells has been isolated from human umbilical cord blood.

In the context of the present invention by "purified" or "pure" cells it is meant a population of cells that comprises at least 80%, and more preferably at least 90%, human mast cells. In some embodiments, the human mast cells are at least 95% pure. In some embodiments, the cell human mast cells are at least 99% pure.

As used herein, the term "differentiated" refers to a state of cells in which the cultured cells maintain all, or a substantial amount of, their specialized structure and function typical of the cell type in vivo. Partially differentiated cells maintain less than a substantial amount of their full complement of specialized structure and/or function.

As used herein, the terms "expression" or "gene expression" refer to transcription of a gene into an RNA product, and optionally to translation into one or more polypeptide sequences. The term "transcription" refers to the process of copying a DNA sequence of a gene into an RNA product, generally conducted by a DNA-directed RNA polymerase using DNA as a template.

As used herein, the term "nucleic acid" refers to a polymer of ribonucleic acids or deoxyribonucleic acids, including RNA, mRNA, rRNA, tRNA, small nuclear RNAs, cDNA, DNA, PNA, RNA/DNA copolymers, or analogues thereof. Nucleic acid may be obtained from a cellular extract, genomic or extragenomic DNA, viral RNA or DNA, or artificially/chemically synthesized molecules.

As used herein, the term "RNA" refers to a polymer of ribonucleic acids, including RNA, mRNA, rRNA, tRNA, and small nuclear RNAs, as well as to RNAs that comprise ribonucleotide analogues to natural ribonucleic acid residues, such as 2-O-methylated residues.

As used herein, the term "phenotype" refers to all the observable characteristics of a cell (or organism); its shape (morphology); interactions with other cells and the non-cellular environment (e.g., extracellular matrix); proteins that appear on the cell surface (surface markers); and the cell's behavior (e.g., secretion, contraction, synaptic transmission).

As used herein, the terms "administer", "apply", "treat", "transplant", "implant", "deliver", and grammatical variations thereof, are used interchangeably to provide mast cells of the invention to a mammal, or, depending upon the context, contacting a potential modulator of biological activity (candidate agent) with a mast cell of the invention.

As used in this specification and the appended claims, the singular forms "a", "an", and "the" include plural reference unless the context clearly dictates otherwise. Thus, for example, a reference to "a mast cell" or "a human mast cell" includes one or more of such cells. Reference to "a potential modulator" or "a candidate agent" includes one or more of such modulators or agents.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Culture of Mast Cells from Human Cord Blood-Derived Hematopoietic Stem Cells

Hematopoietic stem cells were isolated from HUCB using CD133+ bead selection (Miltenyi Biotec). Purified cells were cultured in human stem cell factor (SCF), IL-6, and IL-3 for 14 days. After continued culture in SCF and IL-6 for 6 weeks, single cell cultures were established in 96-well plates using only culture medium and 2% fetal bovine serum (FBS). After 6 months, surviving colonies were examined for expression of mast cell-specific markers.

EXAMPLE 2

Cell Culture Conditions

The LAD2 is a highly differentiated cell human mast cell line derived from a patient diagnosed with mast cell sarcoma and was kindly provided by Dr. A. Kirshenbaum (National Institute of Health, Bethesda, Md.). LAD2 cells were cultured in StemPro-34 media (Gibco) supplemented with (2 mM L-glutamine, 100 IU/ml penicillin, 50 ug/ml streptomycin, human recombinant stem cell factor 100 ng/ml) (PreProtech). Cell culture was performed at 5% $CO_2$-95% air at 37° C. in a humidified atmosphere. For optimal growth, the cell density was maintained between $0.5\times10^5$ and $1\times10^6$ cells/ml. Average doubling time was 2-3 weeks.

The USF-MC1 mast cells were cultured in IMDM (GIBCO) medium supplemented with 2% Fetal bovine serum, 2 mM L-glutamine, 100 IU/ml penicillin, 50 ug/ml streptomycin. Cell culture was performed at 5% $CO_2$-95% air at 37° C. in a humidified atmosphere. For optimal cell growth, the cell density was maintained between 0.5×10E5 and $1\times10^6$ cells/ml. Average doubling time was 1-2 weeks.

EXAMPLE 3

Flow Cytometry

Figure 5A:
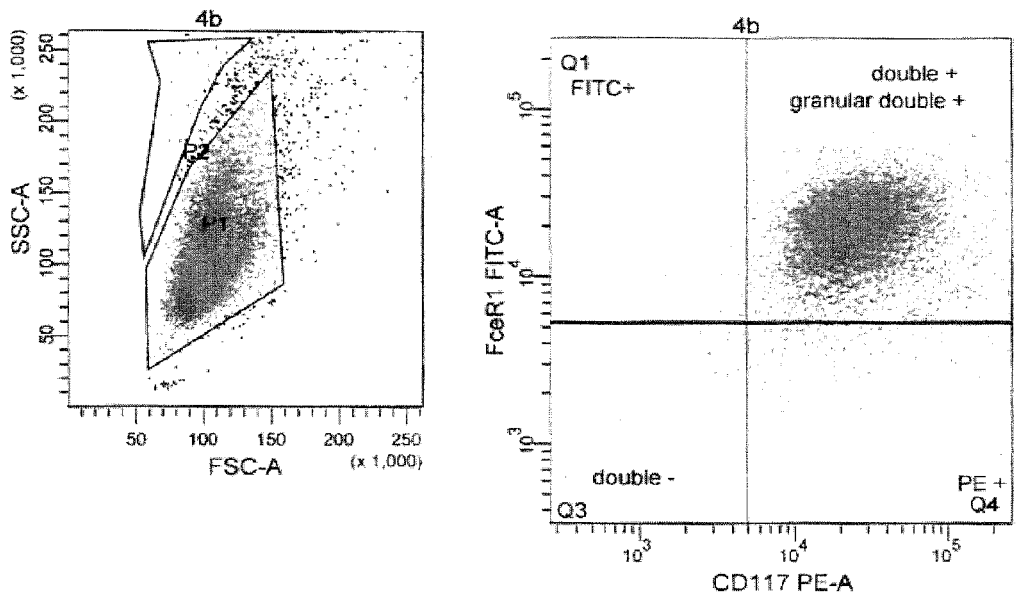
FIGS. 5A-C show results of characterization of USF-MC1 cells transfected with SV40 LT.

To demonstrate the expression of mast cell surface markers, LAD2 and USF-MC1 mast cells were incubated with murine monoclonal antibody against CD117-PE (AbD Serotec) and FceRI-FITC (eBioscience) for 30 minutes at 4° C. Double staining positive cells were analyzed by flow cytometry (FIG. 5A).

EXAMPLE 4

Intracellular Staining for Tryptase and Chymase

Figure 5B:
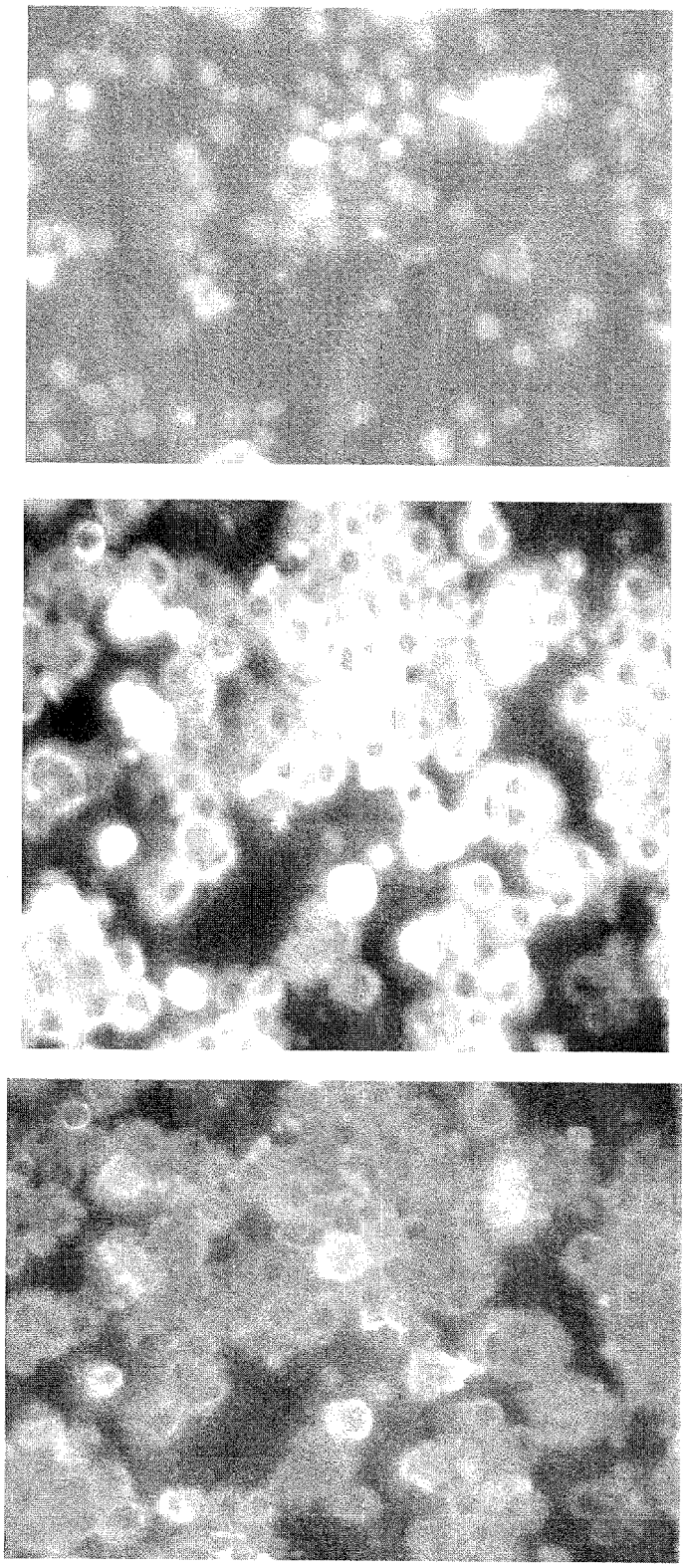

To detect the presence of tryptase and chymase in mast cells, LAD2 and USF-MC1 mast cells were blocked with normal goat serum for 1 h, then incubated with a rabbit anti-human mast cell tryptase polyclonal antibody and a mouse anti-human mast cell chymase monoclonal antibody overnight at 4° C. The cells were washed again in Perm/Wash buffer and incubated for a further 30 minutes at 4° C. in the same buffer containing anti-mouse(FITC) and anti-rabbit (Alexa 555) fluorescent conjugate antibodies. After a final wash with PBS, nuclei were stained with DAPI (Vector Biolabs) and examined by epifluorescent microscopy. Results are shown in FIG. 5B (DAPI only=top panel; chymase=middle panel; tryptase=bottom panel).

EXAMPLE 5

Metachromatic Staining with Toluidine Blue and Alcean Blue

Cells were attached to slides by cytospin centrifugation and fixed with 10% formalin for 20 minutes at RT, then stained in toluidine blue working solution for 2-3 minutes. Slides were washed in distilled water 3 times, then sequentially dehydrated in 100% alcohol, and xylene. For alcian blue staining, the slides were fixed in 3% acetic acid, for 3 minutes, then placed in alcian blue solution for 30 minutes at RT. After slides were washed in distilled water for 2 minutes, slides were stained with nuclear-fast red for 5 minutes, then washed and dehydrated in alcohol and coverslips were attached.

EXAMPLE 6

Intracellular Staining for Myeloperoxidase

Mast cells were attached to slides by cytospin centrifugation and fixed with cold (4° C.) buffered formalin-acetone for 30 sec. Slides were washed in water and incubated at RT for 15 minutes in staining medium (3,3,-diaminobenzidine (20 mg) in 50 ml tris-HCL buffer+0.2 ml 3% H2O2). Slides were washed in tap water, counterstained with Wright/Giemsa and coverslips were attached.

EXAMPLE 7

Activation of Mast Cells and Measurement of Beta-Hexosaminidase Release

Figure 5C:
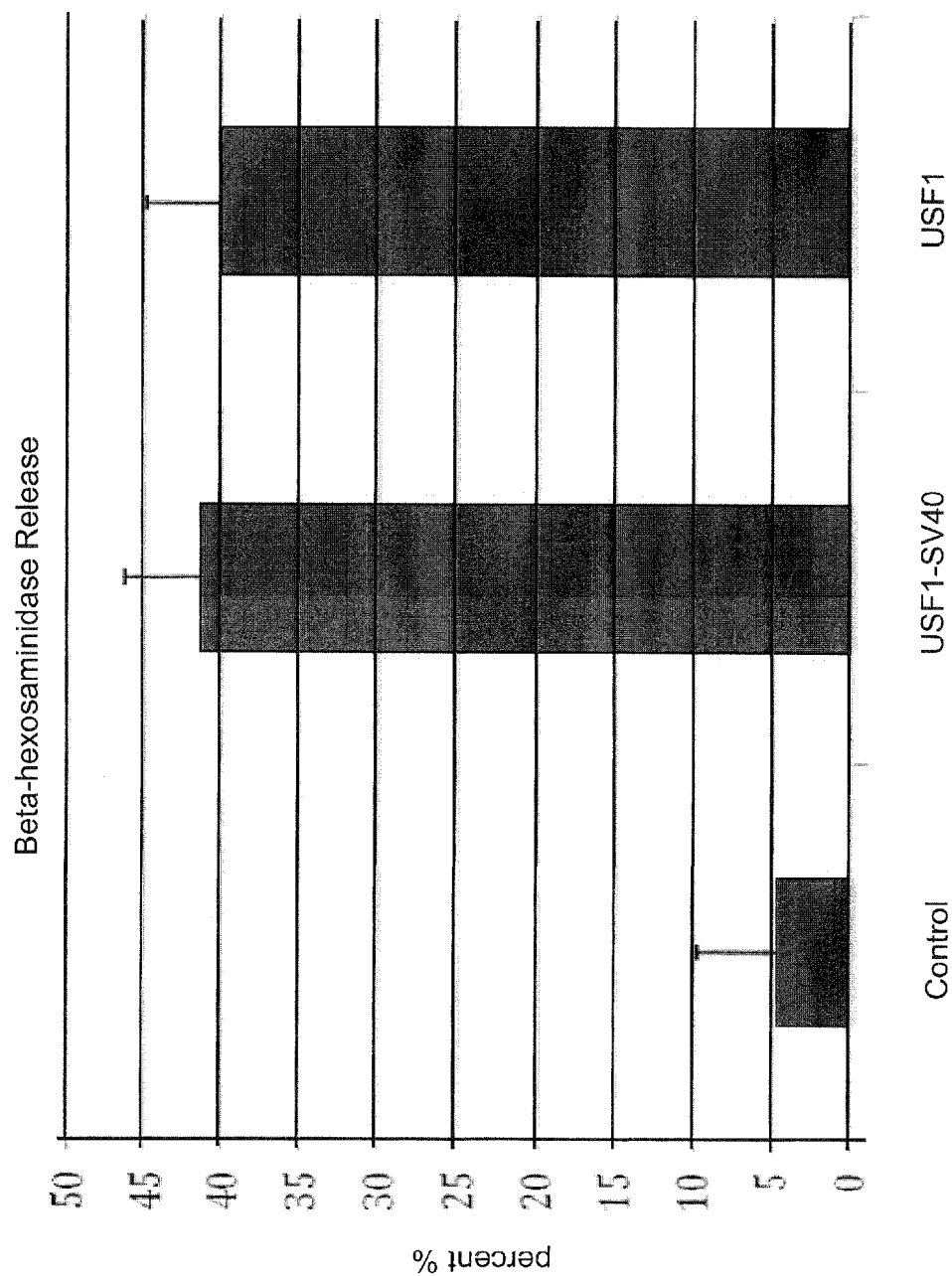

In order to activate mast cells via the FceR1 receptor, cells were cultured for 18 hours with biotinylated human myeloma IgE (100 ng/ml)(Sigma). Cells were then challenged with streptavidin (100 ng/ml)(Sigma), ionomycin (5 μM), or atrial natriuretic peptide (ANP) (100 ng/ml). After 30 minutes, supernatants and cell pellets were harvested. Substrate solution (p-Nitrophenyl-N-acetyl-B-D-glucosaminide Calbiochem, 0.13% in sodium citric solution) was added to either the cell supernatants or pellets and incubated for 1.5 hr. 0.4M glycine solution was then added to stop the reaction. The optical density (OD) was read at 405 nm. Percent release was expressed as a ratio of supernatant over total (supernatant+lysate). Percent release of beta-hexosadminidase by SV40 LT-transfected USF-MC1 cells and non-transfected USF-MC1 cells is shown in FIG. 5C.

EXAMPLE 8

Enzyme-Linked Immunosorbent Assay (ELISA) for TNF-a, IL-17, and Leukotriene C4

TNF-a (R&G Systems), IL-17 (eBioscience), and Leukotrine C4 (Cayman Chemical) protein concentrations in mast cell supernatants were determined using ELISA kits from each respective manufacturer. Each ELISA was performed according to the manufacturer's instructions.

EXAMPLE 9

Quantitative Real Time PCR (qPCR)

Total RNA was isolated by QIAGEN (RNeasy) isolation kit using the manufacturer's instructions. Reverse transcription reaction was performed using random hexamers and Superscript III (Invitrogen). Quantitative real-time RT-PCR was performed by using the ABI/PRISM 7900 HT Sequence Detection system (Applied Biosystems). Transcripts were quantified using the house keeping gene glyceraldehyde 3-phosphate dehydrogenase (GAPDH) as control. The primers used are listed in Table 1 and SYBER Green (SuperArray) was used as the fluorescent reporter dye. Quantification of expression of the target gene in samples was accomplished by measuring the fractional cycle number at which the amount of expression reaches a fixed threshold ($C_T$). The relative quantification was given by the $C_T$ values determined for triplicate reactions for test and reference samples for each target and for GAPDH. Triplicate $C_T$ values were averaged and the GAPDH $C_T$ subtracted to obtain $\Delta C_T$. Relative expression level of target gene was determined as $2^{-\Delta C_T}$

```
The primer of LT forward:
                              (SEQ ID NO: 1)
5' TAGATTCCAACCTATGGAACTAT 3':
and reverse:
                              (SEQ ID NO: 2)
5' GGAAAGTCCTTGGGGTCTTCTACC 3'.
```

EXAMPLE 10

SV40 LT Transfection of USF-1 Cells

USF-MC1 mast cells were transfected with pCMV-SV40-LT using Lipofectamine 2000 plus reagent (Invitrogen). Twenty-four hours later, transfected cells were selected in culture medium supplemented with 0.5 mg/ml G418(Gibco BRL). G418 resistant cells were grown in culture and expression of LT was confirmed by RT-PCR.

EXAMPLE 11

Statistical Analysis

All experiments were done in triplicate. Pairs of groups were compared by Students t-Test. Differences between groups were considered significant at $p<0.05$. Data for all measurements are expressed as means±s.d.

EXAMPLE 12

Derivation of USF-1 Cell Line from Cord Blood Cells

Human umbilical cord blood stem cells HCBSC positively selected for CD133+ were cultured in IL-3, IL-6, and SCF for 2 weeks followed by a six week culture in the presence or absence of SCF and IL-6 for 6 weeks. From this population, single cell cultures were established in 96-well plates using only culture medium and 2% fetal bovine serum (FBS). Of ten surviving colonies, one expressed both FceR1 and CD117 on its surface by flow cytometry. FIG. 1A shows flow cytometry scatter plots. The top panel shows HCBSC cultured for 2 weeks in IL-3, IL-6 and SCF for 2 weeks then cultured in the absence (upper panel) or presence (lower panel) of SCF and IL-6.

Immunocytochemistry revealed uniform expression of tryptase with 30% chymase staining. In both USF-MC1 and the established human mast cell line LAD2, IgE cross-linking, ionomycin, and ANP-challenge induced 30 to 50% B-Hex release at 1 hr and 5-15 fold increase in LTC4 release at 6 hr. ANP-induced release of both B-Hex and LTC4 was reduced to baseline by isatin, an ANP receptor antagonist. Cytokine expression was induced by IgE and non-immunologic stimuli in a similar fashion in both LAD2 and USF-MC1. USF-MC1 was successfully transfected with SV40 LT with retained expression of tryptase, chymase, FceR1, CD117, and ability to release histamine.

Stem cells cultured in the absence of SCF and IL-6 demonstrate staining only for CD117. Stem cells cultured in the presence of SCF and IL-6 demonstrate double staining for the IgE receptor, FceR1 and CD117 (cKIT).

Flow cytometry of single cell-derived USF-MC1 cells cultured for 12 weeks in the absence of SCF and IL-6. Despite the absence of SCF and IL-6 for 12 weeks, USF-MC1 cells stain positively for FceR1 and CD117.

EXAMPLE 13

Immunofluorescent Staining of USF-MC1 Cells for Mast Cell-Specific Markers

Figure 2A:
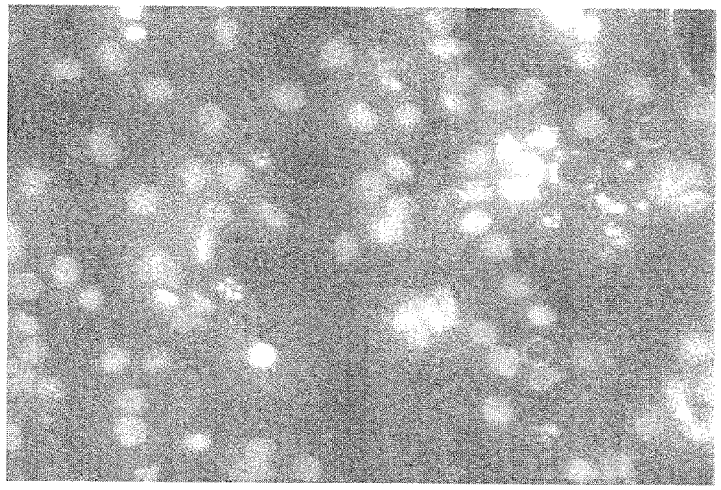
FIG. 2A-C show staining of USF-MC1 cells for mast cell-specific markers.
Figure 2A:
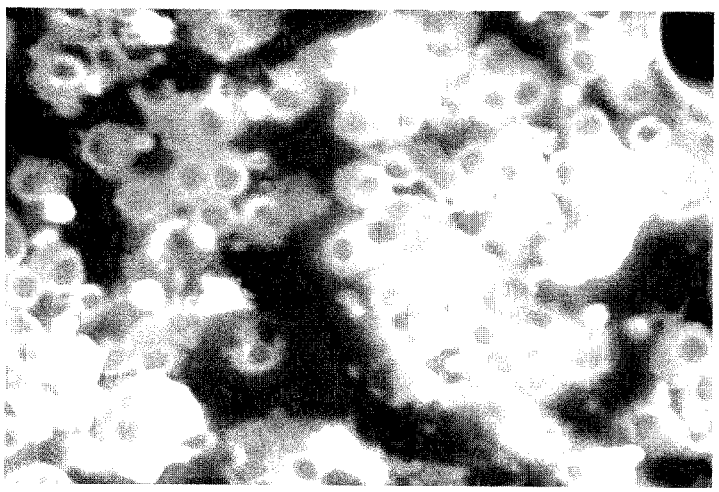
Figure 2A:
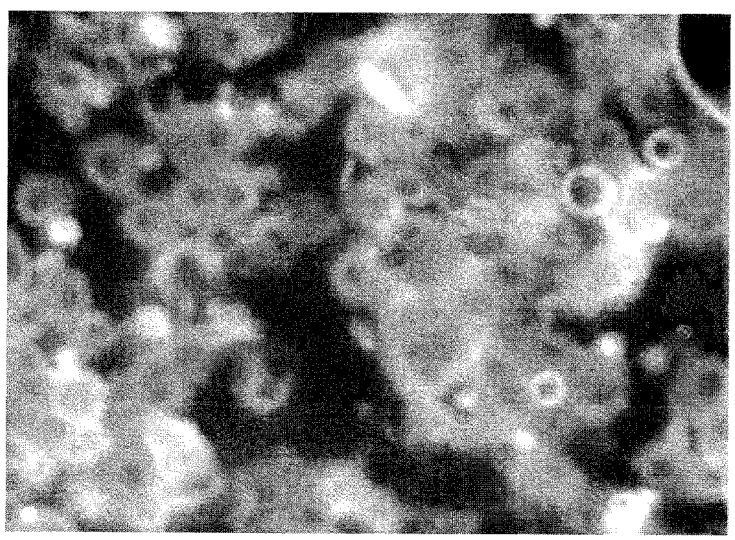
Figure 2B:
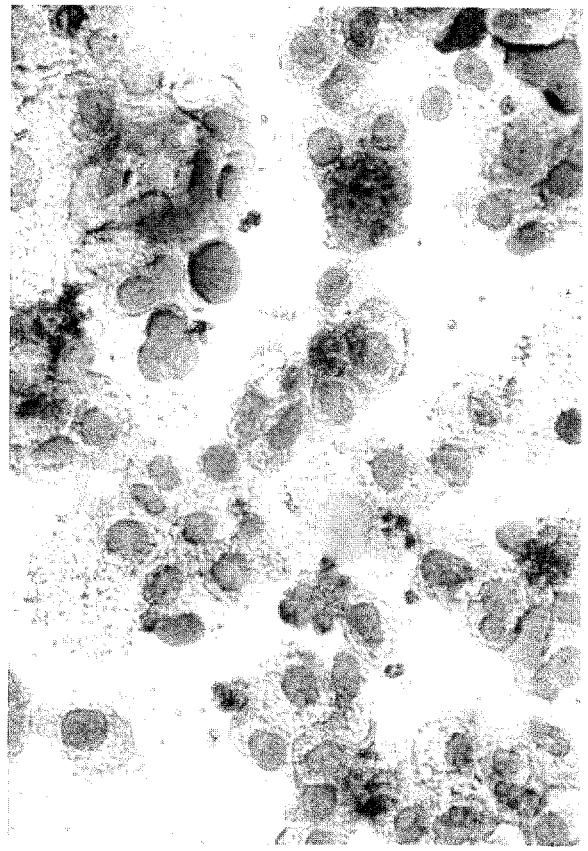
Figure 2B:
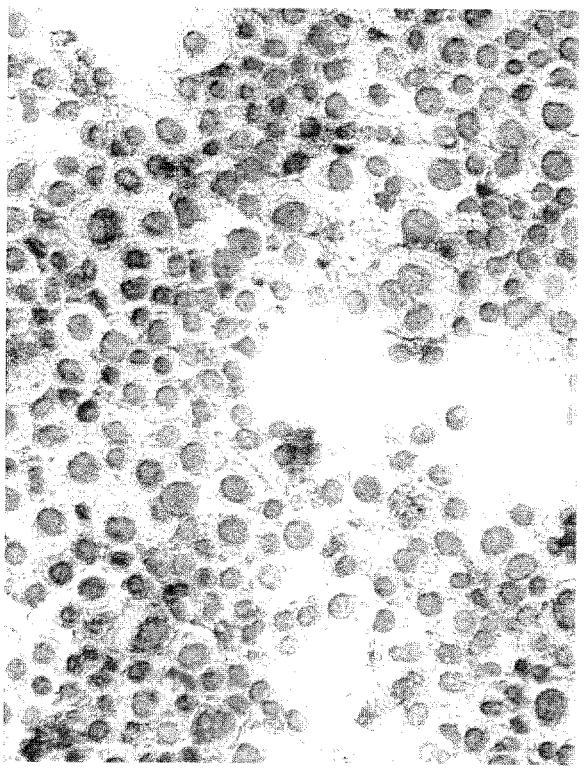
Figure 2C:
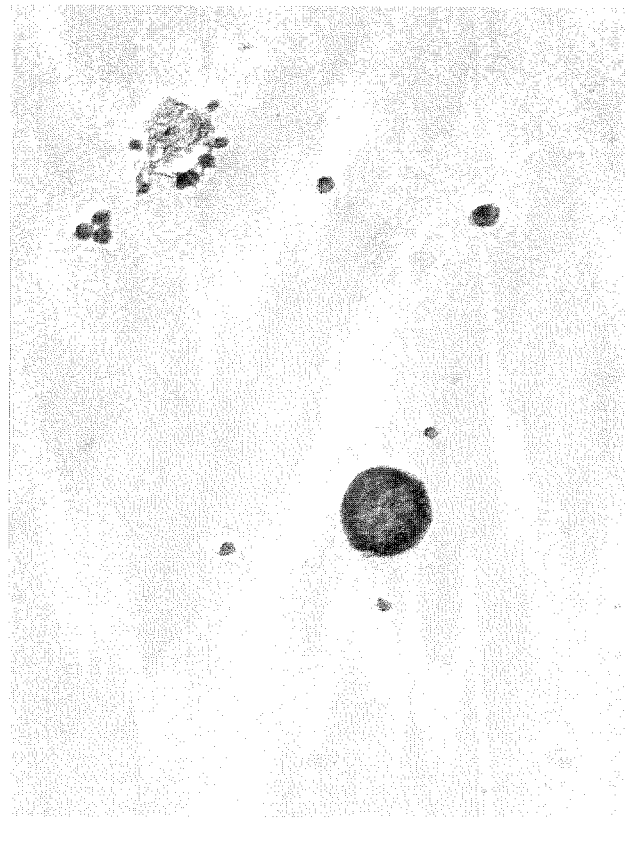
Figure 2C:
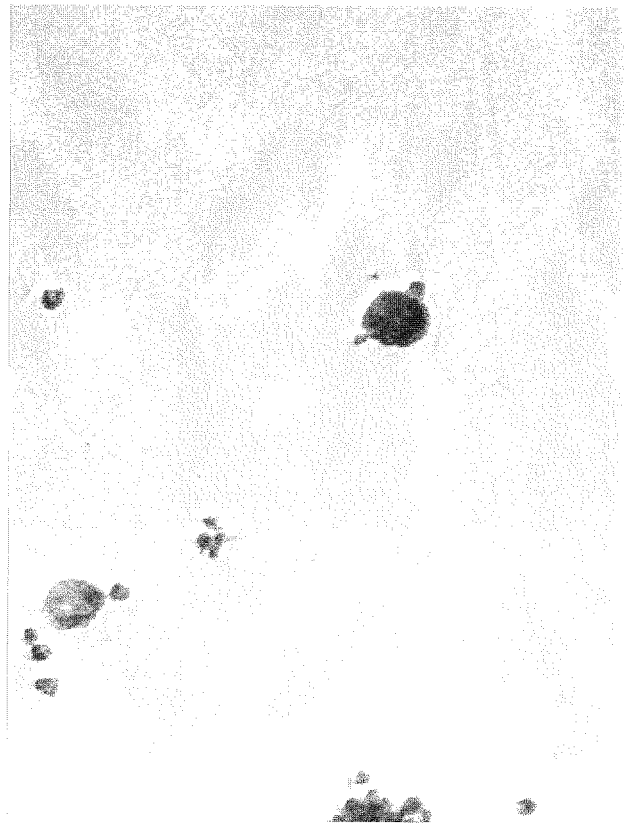
Figure 3A:
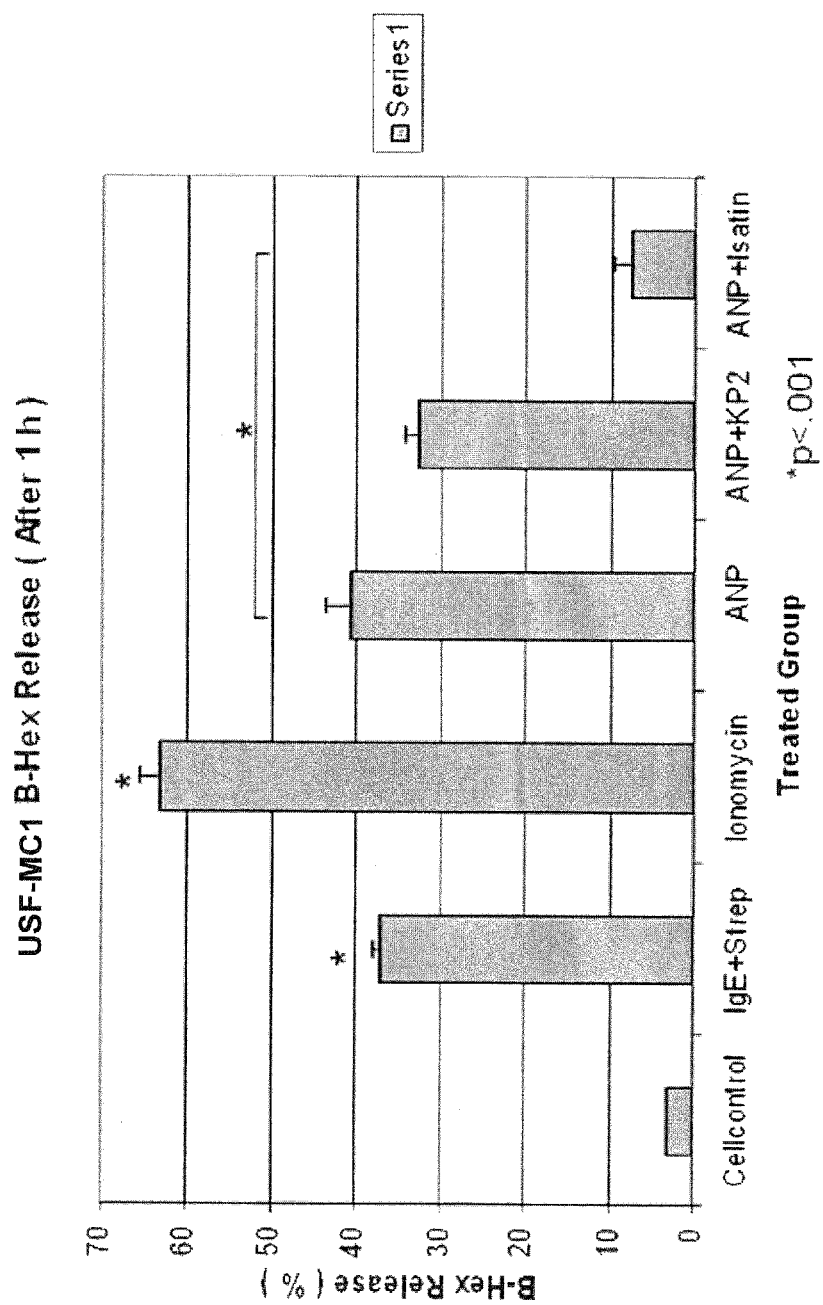
FIGS. 3A-D show graphs of histamine (beta hexosaminidase) release from USF-MC1 cells compared to LAD2 cells after one hour (FIGS. 3A and 3B, respectively), and after six hours (FIGS. 3D and 3C, respectively). USF-MC1 cells (2×106 per well) were coated with biotinylated human myeloma IgE for 18 hours. Cells were then washed and challenged with streptavidin (100 ng/ml), ionomycin (5 μM), ANP (1 μM), ANP+KP2, ANP+Isatin. After 30 minutes, supernatants and cell lysates were developed with N-acetyl-B-D-glucosaminidase and optical density (OD) was read at 405 nm. Percent release is expressed as a ratio of supernatant over total (supernatant+lysate). These results indicate that USF-MC1 releases histamine within minutes following activation of the IgE receptor, direct calcium influx (ionomycin) and activation of the natriuretic peptide receptor A (NPRA) (ANP). In addition, ANP-induced histamine release is attenuated by an NPRA receptor antagonist (isatin).
Figure 3B:
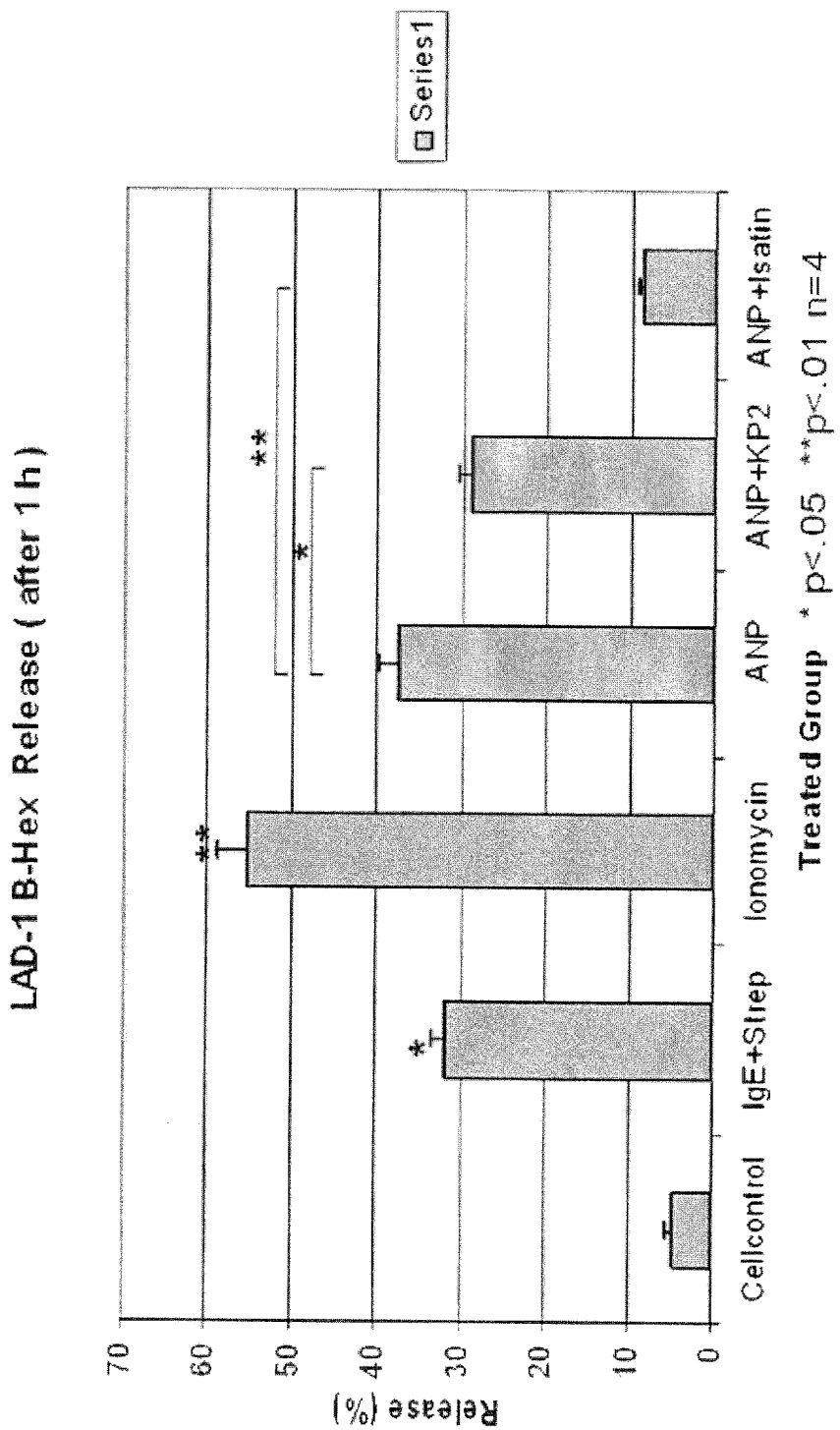
Figure 3C:
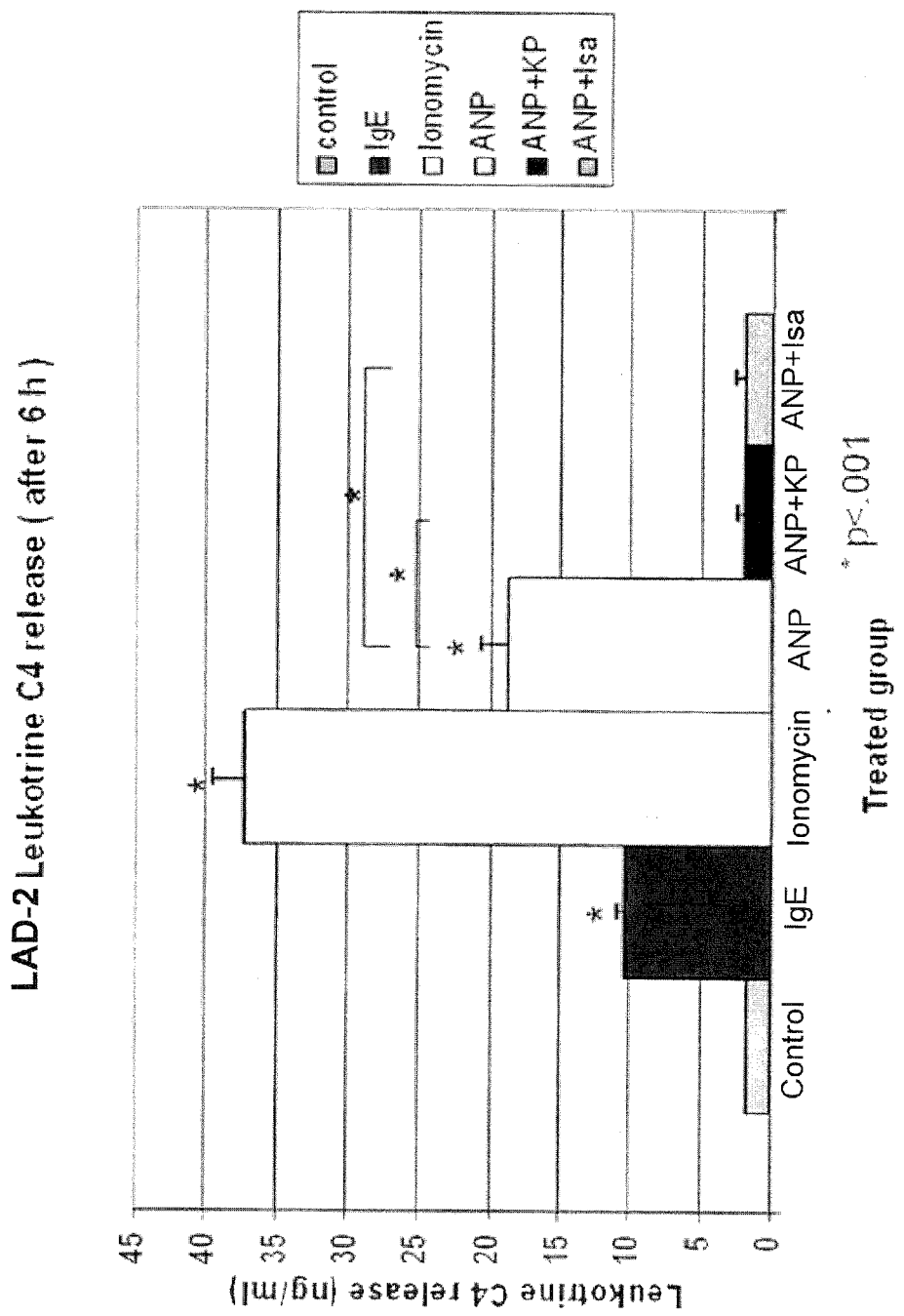
Figure 3D:
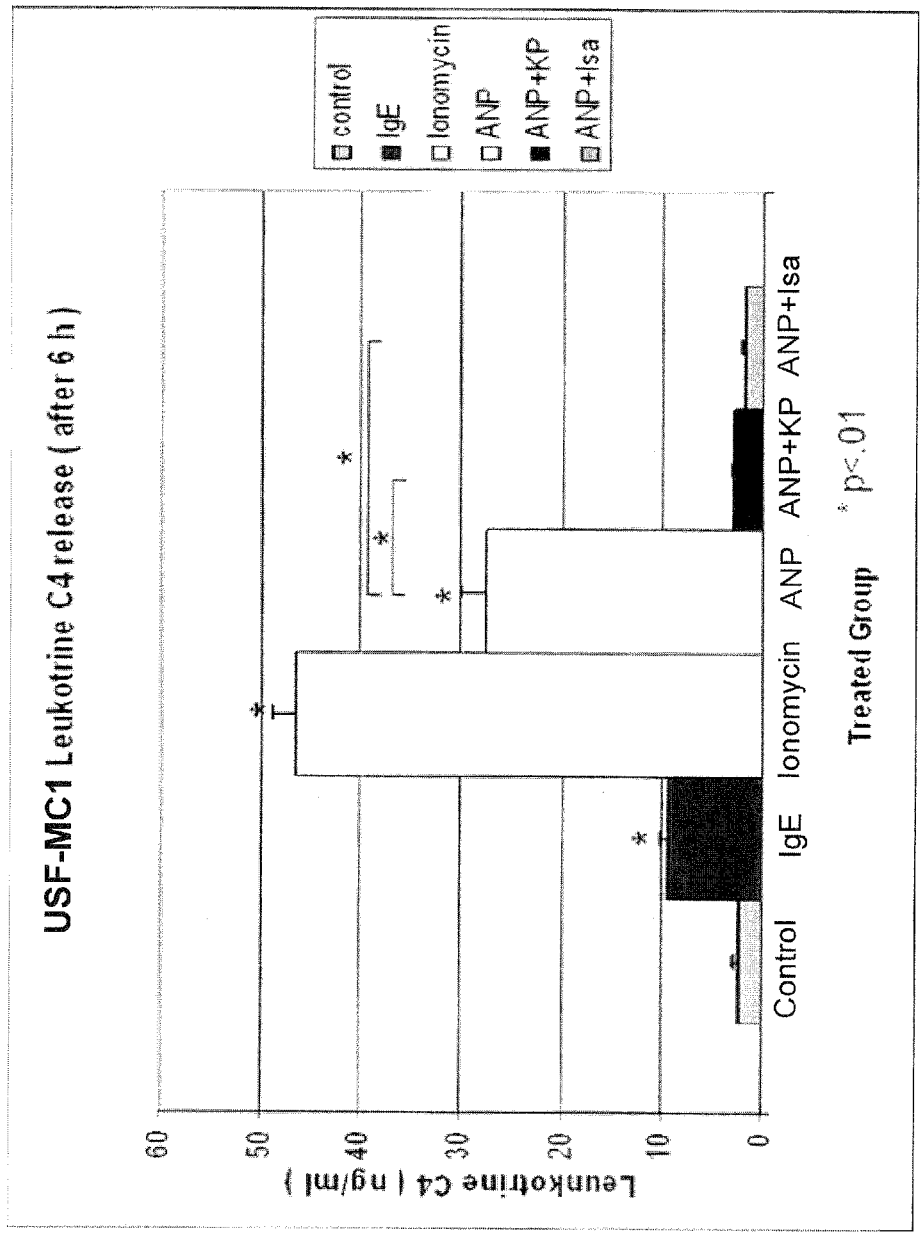

Cells were stained with the nuclear stain DAPI (blue) and secondary antibodies for tryptase (green) and chymase (red). Negative controls are not shown. USF-MC1 cells stained the nuclear stain DAPI (blue) and chymase (red) (FIG. 2A). The panel shows double staining for DAPI and chymase.

EXAMPLE 14

Histamine (Beta Hexosaminidase) Release from USF-MC1 Cells

USF-MC1 cells ($2 \times 10^6$ per well) were coated with biotinylated human myeloma IgE for 18 hours. Cells were then washed and challenged with streptavidin (100 ng/ml), ionomycin (5 µM), ANP (1 µM), ANP+KP2, ANP+Isatin. After 30 minutes, supernatants and cell lysates were developed with N-acetyl-B-D-glucosaminidase and optical density (OD) was read at 405 nm. Percent release is expressed as a ratio of supernatant over total (supernatant+lysate). These results indicate that USF-MC1 releases histamine within minutes following activation of the IgE receptor, direct calcium influx (ionomycin) and activation of the NPRA receptor (ANP). In addition, ANP-induced histamine release is attenuated an NPRA receptor antagonist (isatin). Results are shown in FIGS. 3A-D.

EXAMPLE 15

USF-MC1 and LAD-2 Show Similar Cytokine Release Profile

Figure 4A:
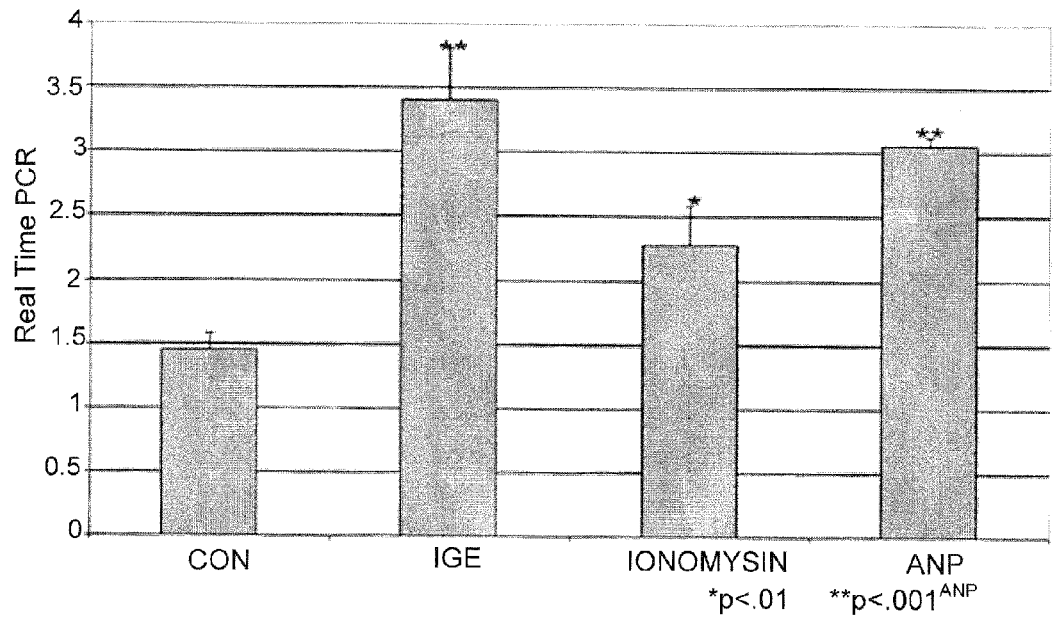
FIGS. 4A-D show cytokine cytokine release profiles of USF-MC1 cells compared to LAD2 cells.
Figure 4A:
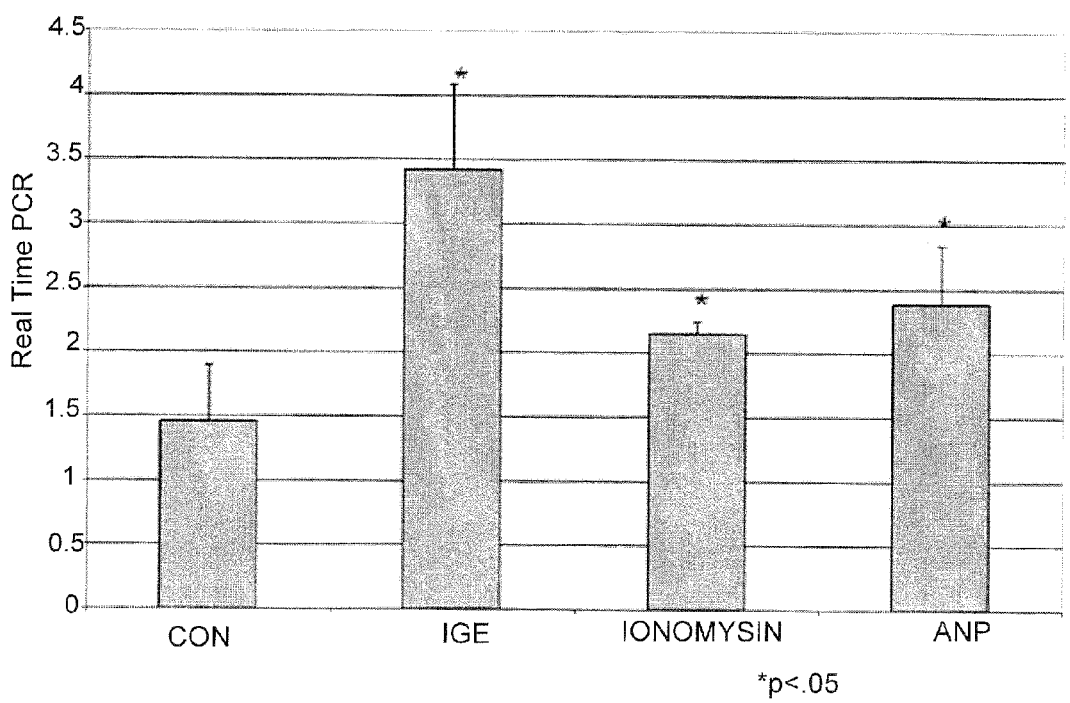
Figure 4B:
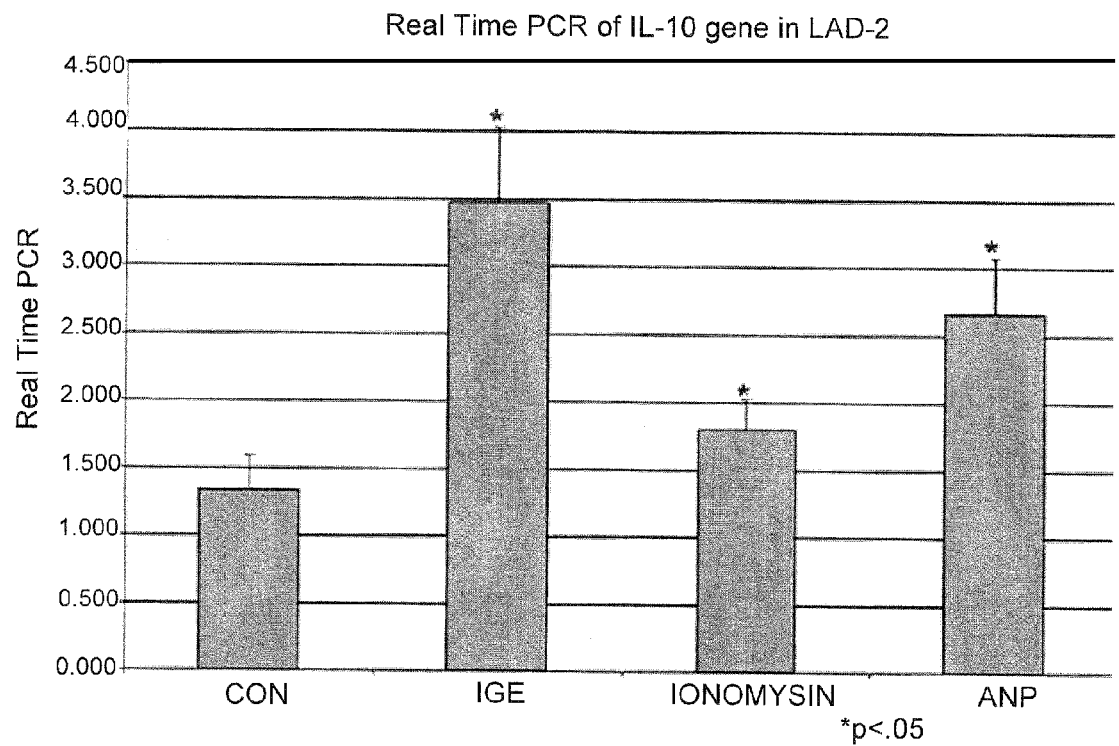
Figure 4B:
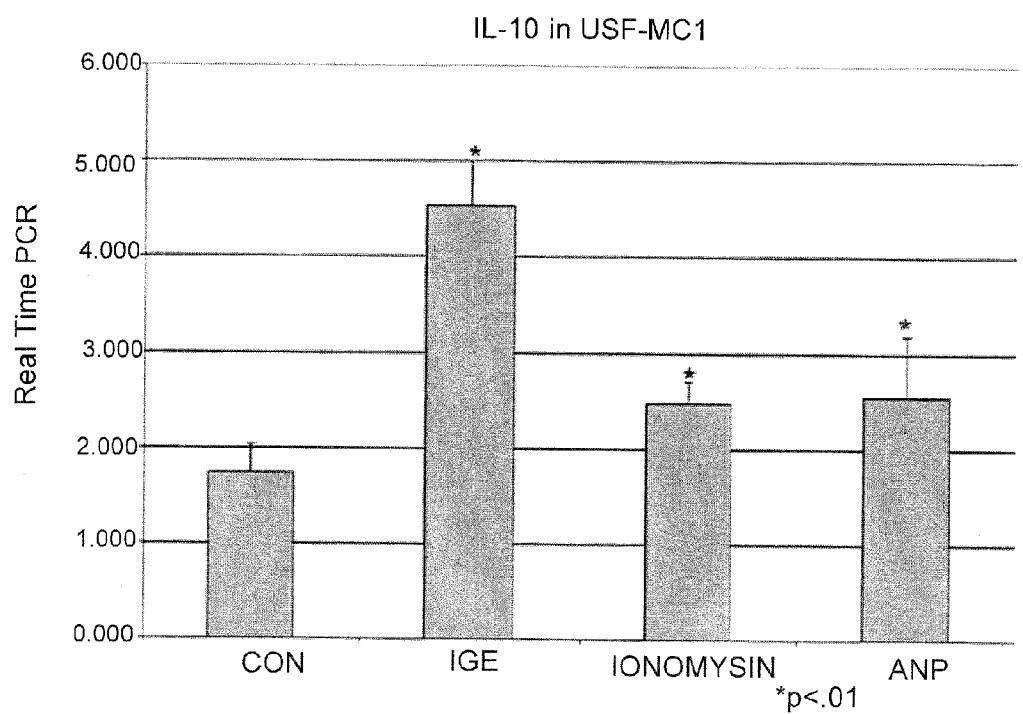

Cells were cultured in presence of IgE stimulation or stimulation by ionomycin and cytokines released were examined. The cytokines examined included IL-12 receptor beta 2 (FIG. 4A), IL-10 (FIG. 4B), TSLP (data not shown), TNFSF4

Figure 4C:
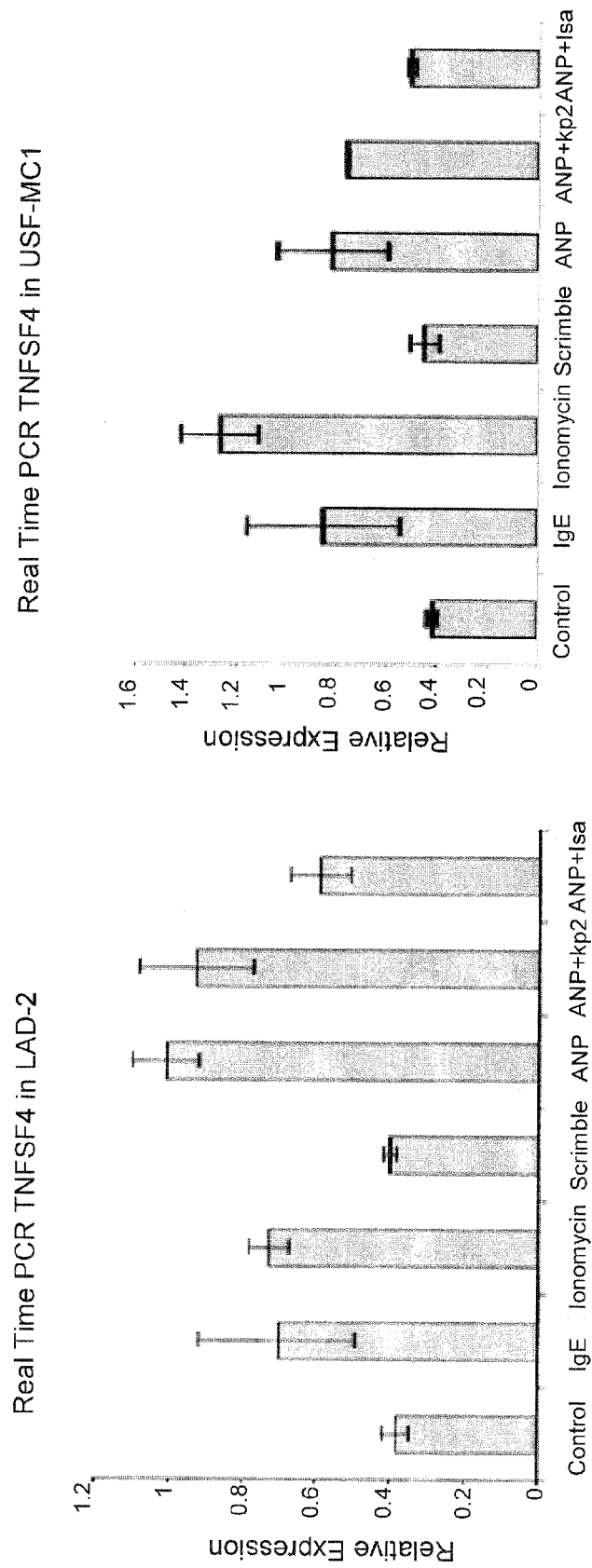
Figure 4D:
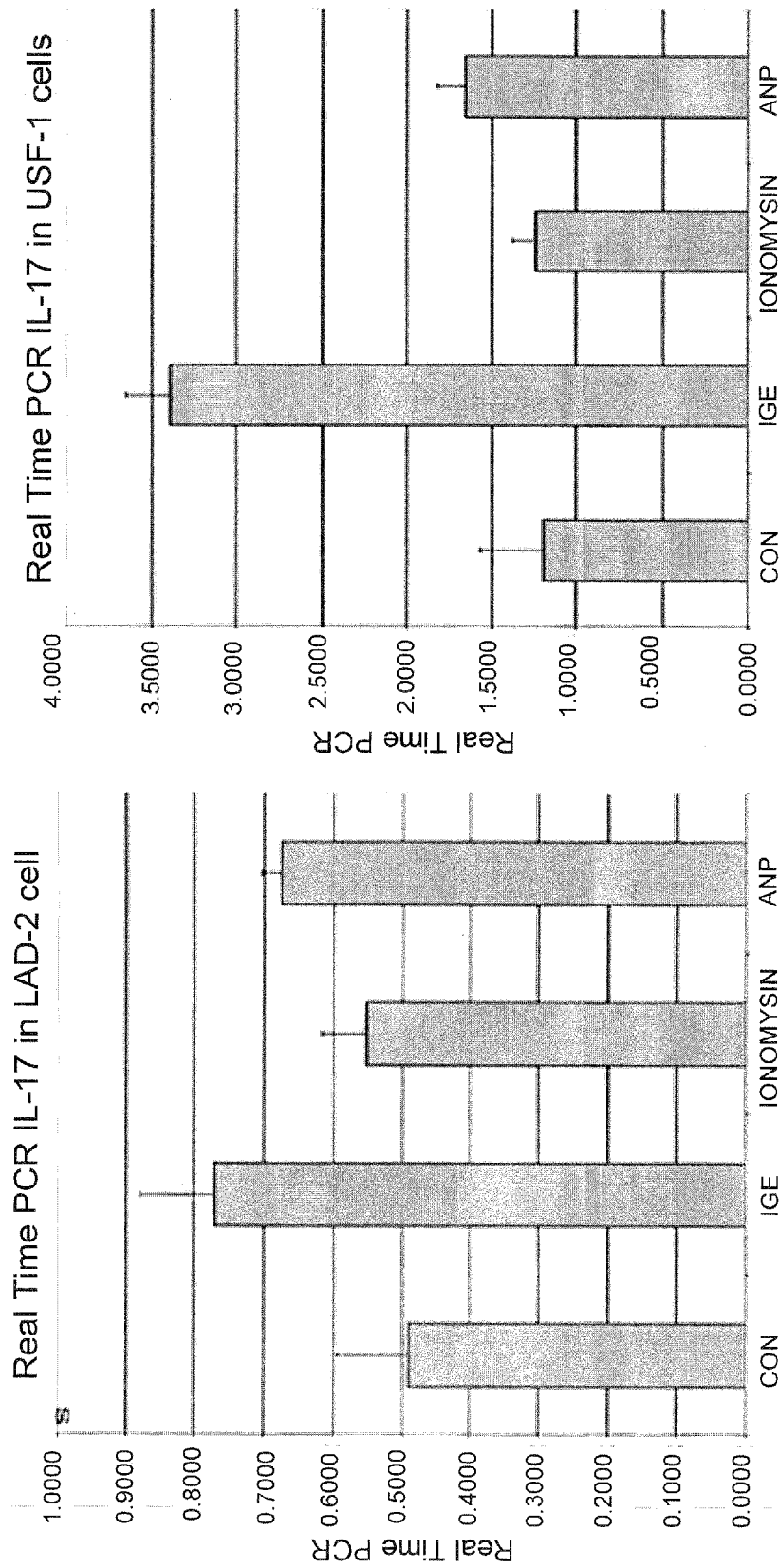

(FIG. 4C), and IL-17 (FIG. 4D). The cytokine levels were examined using PCR technique as described using primers listed in Table 1. The results show that the patterns were similar for both LAD2 and USF-MC1 cell line.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

| Target Gene | Primers |
| --- | --- |
| IL-10 | Sense 5'-GCTGGAGGACTTTAAGGGTTACCT-3' (SEQ ID NO: 3)<br>Antisense 5'-CTTGATGTCTGGGTCTTGGTTCT-3' (SEQ ID NO: 4) |
| IL-12 receptor beta 2 | Sense 5'-TCCGACCCAAAGCCCGAAA-3' (SEQ ID NO: 5)<br>Antisense 5'-TTCCAGAGAGTCAGCGAGAGGT-3' (SEQ ID NO: 6) |
| TSLP | Sense: 5'-TATGAGTGGGACCAAAAGTACCG-3' (SEQ ID NO: 7) |

TABLE 1-continued

| Target Gene | Primers |
| --- | --- |
| | Antisense: 5'-GGGATTGAAGGTTAGGCTCTGG-3' (SEQ ID NO: 8) |
| TNFSF4 | Sense 5'-CCTGGAAGAGAATGTGGGAAATGC-3' (SEQ ID NO: 9)<br>Antisense 5'-CCGATGTGATACCTGAAGAGCAGA-3' (SEQ ID NO: 10) |
| IL-17 | Sense 5'-AGTGTAGGAACTTGGGCTGC-3' (SEQ ID NO: 11)<br>Antisense 5'-AGGGTCTCTTGCTGGATGGGAA-3' (SEQ ID NO: 12) |

Any patents, patent applications, provisional applications, and publications that have been referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The invention claimed is:

1. A human umbilical cord blood mast cell, wherein the mast cell has been genetically modified with a nucleic acid sequence encoding SV40 Large T antigen, and wherein the mast cell expresses the FceR1 receptor and CD117 and releases histamine.

2. The mast cell of claim 1, wherein the mast cell has one or both of the following characteristics: expresses tryptase and expresses chimase.

3. The mast cell of claim 2, wherein the mast cell has both of the following characteristics: expresses tryptase, and expresses chimase.

4. The mast cell of claim 1, wherein the genetic modification is transfection.

5. The mast cell of claim 1, wherein the mast cell expresses the FceR1 receptor and CD117 in the absence of human stem cell factor (SCF).

6. A composition comprising human umbilical cord blood mast cells, wherein the mast cells have been genetically modified with a nucleic acid sequence encoding SV40 Large T antigen, and wherein the mast cells express the FceR1 receptor and CD117 and release histamine.

7. The composition of claim 6, wherein said composition is a cell culture, further comprising culture medium.

8. The composition of claim 6, wherein the mast cell has one or both of the following characteristics: expresses tryptase, and expresses chimase.

9. The composition of claim 8, wherein the mast cell has both of the following characteristics: expresses tryptase.

10. The composition of claim 6, wherein the mast cell expresses the FceR1 receptor and CD117 in the absence of human stem cell factor (SCF).

11. A method for obtaining human mast cells, comprising genetically modifying human mast cells with a nucleic acid sequence encoding SV40 Large T antigen, wherein prior to said modifying, the human mast cells are obtained by separating hematopoietic stem cells from human umbilical cord blood, culturing the stem cells for a period of time, and establishing single cell cultures comprising one or more colonies of human mast cells, and wherein the genetically modified mast cells express the FceR1 receptor and CD117 and release histamine.

12. The method of claim 11, wherein the separated hematopoietic stem cells are cultured in the presence of human stem cell factor (SCF), IL-6, and IL-3.

13. A method for identifying modulators of human mast cell survival, function or phenotypic expression comprising: (a) determining survival, function or phenotypic expression, of human mast cells in the presence of a potential modulator, wherein the human mast cells are obtained from human umbilical cord blood, genetically modified with a nucleic acid sequence encoding SV40 Large T antigen and wherein the mast cells express the FceR1 receptor and CD117 and release histamine; and (b) comparing the determined survival, function or phenotypic expression to the human mast cells in the absence of the potential modulator, wherein the modulator is identified by an increase or decrease in survival, function or phenotypic expression of the human mast cells in its presence.

14. A method for identifying agents that modulate activation of mast cells, comprising (a) contacting a human umbilical cord blood mast cell with a candidate agent, wherein the mast cell has been genetically modified with a nucleic acid sequence encoding SV40 large T antigen, expresses the FceR1 receptor and CD117, and releases histamine, and (b) determining activation of the mast cell in the presence of the candidate agent, and (c) comparing the determined activation of the mast cell in the presence of the candidate agent to the activation of the mast cell in the absence of the candidate agent, wherein the modulator is identified by an increase or decrease in activation of the mast cell in its presence.

15. A method for identifying modulators of human mast cell migration, comprising: (a) determining migration of human mast cells in the presence of a potential migration modulator, wherein the human mast cells have been obtained from human umbilical cord blood and genetically modified with a nucleic acid sequencing encoding SV40 Large T antigen; and (b) comparing the migration of the mast cells to migration of the cells in the absence of the potential modulator, wherein the modulator is identified by an increase or decrease in migration of the human mast cells in its presence, wherein the mast cells express the FceR1 receptor and CD117 and release histamine.

16. A method for identifying modulators of human mast cell proliferation, comprising: (a) determining proliferation of human mast cells in the presence of a potential proliferation modulator, wherein the human mast cells have been obtained from human umbilical cord blood and genetically modified with a nucleic acid sequence encoding SV40 Large T antigen; and (b) comparing the proliferation of the mast cells to proliferation of the cells in the absence of the potential modulator, wherein the modulator is identified by an increase or decrease in proliferation of the human mast cells in its presence, and wherein the mast cells express the FceR1 receptor and CD117 and release histamine.

17. A method for transplanting human mast cells, comprising administering human mast cells to a mammal, wherein the mast cells have been obtained from human umbilical cord blood and genetically modified with a nucleic acid sequence encoding SV40 Large T antigen, and wherein the mast cells express the FceR1 receptor and CD117 and release histamine.

18. The method of claim 17, wherein the mammal is human, and the transplanted mast cells are autologous to the human.

* * * * *

UNITED STATES PATENT AND TRADEMARK OFFICE
CERTIFICATE OF CORRECTION

| | |
|---|---|
| PATENT NO. | : 9,096,829 B2 |
| APPLICATION NO. | : 13/255599 |
| DATED | : August 4, 2015 |
| INVENTOR(S) | : Shyam S. Mohapatra, Mark Glaum and Guoqing Liu |

It is certified that error appears in the above-identified patent and that said Letters Patent is hereby corrected as shown below:

In the Specification

<u>Column 3,</u>
Line 45, "deter mining" should read --determining--.

<u>Column 10,</u>
Line 26, "ST1571" should read --STI571--.

<u>Column 12,</u>
Line 61, "Fat mulations" should read --Formulations--.

Signed and Sealed this
Twenty-first Day of June, 2016

Michelle K. Lee
*Director of the United States Patent and Trademark Office*